(12) United States Patent
Linford et al.

(10) Patent No.: US 9,164,068 B2
(45) Date of Patent: **\*Oct. 20, 2015**

(54) THIN LAYER CHROMATOGRAPHY PLATES AND RELATED METHODS

(75) Inventors: Matthew R. Linford, Orem, UT (US); Robert C. Davis, Provo, UT (US); Richard R. Vanfleet, Provo, UT (US); David Scott Jensen, Provo, UT (US); Li Yang, Richland, WA (US); Jun Song, Clifton Park, NY (US)

(73) Assignee: BRIGHAM YOUNG UNIVERSITY, Provo, UT (US)

(\*) Notice: Subject to any disclaimer, the term of this patent is extended or adjusted under 35 U.S.C. 154(b) by 161 days.

This patent is subject to a terminal disclaimer.

(21) Appl. No.: 12/958,595

(22) Filed: Dec. 2, 2010

(65) Prior Publication Data

US 2011/0089096 A1  Apr. 21, 2011

Related U.S. Application Data

(63) Continuation-in-part of application No. 12/826,940, filed on Jun. 30, 2010.

(60) Provisional application No. 61/270,023, filed on Jul. 1, 2009, provisional application No. 61/283,281, filed on Dec. 2, 2009.

(51) Int. Cl.
*G01N 30/92* (2006.01)
*B01J 20/28* (2006.01)
(Continued)

(52) U.S. Cl.
CPC ............... *G01N 30/92* (2013.01); *B01J 20/282* (2013.01); *B01J 20/286* (2013.01); *B01J 20/28007* (2013.01); *B82Y 30/00* (2013.01); *G01N 30/93* (2013.01)

(58) Field of Classification Search
CPC .. B01J 20/28007; B01J 20/282; B01J 20/286; G01N 30/93; G01N 30/92; B82Y 30/00
USPC ................. 210/658, 198.2; 73/61.54; 422/70; 436/162
See application file for complete search history.

(56) References Cited

U.S. PATENT DOCUMENTS 4,276,061 A \* 6/1981 Nestrick et al. ................... 95/88
6,749,814 B1   6/2004 Bergh et al.
(Continued)

FOREIGN PATENT DOCUMENTS

CN         1970128      5/2007
CN         102472733    5/2012
(Continued)

OTHER PUBLICATIONS

International Search Report and Written Opinion from International Appliction No. PCT/US2011/026313 dated May 30, 2011.
(Continued)

*Primary Examiner* — Ernest G Therkorn
(74) *Attorney, Agent, or Firm* — Dorsey & Whitney LLP

(57) ABSTRACT

In an embodiment, a method for manufacturing a thin layer chromatography ("TLC") plate is disclosed. The method includes forming a layer of elongated nanostructures (e.g., carbon nanotubes), and at least partially coating the elongated nanostructures with a coating. The coating includes a stationary phase and/or precursor of a stationary phase for use in chromatography. At least a portion of the elongated nanostructures may be removed after being coated. Embodiments for TLC plates and related methods are also disclosed.

14 Claims, 27 Drawing Sheets

(51) Int. Cl.
*B01J 20/282* (2006.01)
*B01J 20/286* (2006.01)
*B82Y 30/00* (2011.01)
*G01N 30/93* (2006.01)

(56) References Cited

U.S. PATENT DOCUMENTS

| | | | |
|---|---|---|---|
| 6,858,434 B1 | 2/2005 | Williams | |
| 7,413,723 B2* | 8/2008 | Niu et al. | 423/447.3 |
| 7,807,557 B2 | 10/2010 | Yoshida et al. | |
| 8,038,887 B2* | 10/2011 | Bakajin et al. | 210/652 |
| 2005/0176245 A1 | 8/2005 | Melechko et al. | |
| 2006/0159916 A1 | 7/2006 | Dubrow et al. | |
| 2007/0193934 A1 | 8/2007 | Shukla et al. | |
| 2007/0237681 A1 | 10/2007 | Boyle et al. | |
| 2008/0223795 A1* | 9/2008 | Bakajin et al. | 210/767 |
| 2009/0085426 A1 | 4/2009 | Davis et al. | |
| 2009/0086923 A1 | 4/2009 | Davis et al. | |
| 2009/0320991 A1* | 12/2009 | Boyle et al. | 156/151 |
| 2010/0285271 A1 | 11/2010 | Davis et al. | |
| 2011/0000852 A1 | 1/2011 | Linford et al. | |
| 2011/0192779 A1 | 8/2011 | Linford et al. | |

FOREIGN PATENT DOCUMENTS

| | | |
|---|---|---|
| WO | WO 2004/059298 | 7/2004 |
| WO | WO 2008/048247 | 4/2008 |
| WO | WO 2008/097360 | 8/2008 |
| WO | WO 2011/002844 | 1/2011 |
| WO | WO 2011/106694 | 9/2011 |

OTHER PUBLICATIONS

Brinkman et al: "Stationary phases for high-performance thin-layer chromatography" Journal of Chromatography, vol. 198, No. 4, 1980—pp. 421-428.

Brinkman et al: "Thin-layer chromatography on chemically bonded phases: a comparison of pre-coated plates", Journal of Chromatography, vol. 258, 1983—pp. 43-55.

Luong et al: "Electrophoretic separation of aniline deriviatives using fused silica capillaries coated with acid treated single-walled carbon nanotubes", Journal of Chromatography, vol. 1074, No. 1-2, 2005—pp. 187-194.

Zhang et al: "Analysis of channel-geometry effects on separation efficiency in rectangular-capillary electrochromatography columns" Journal of Chromatography A, 869 (2000) 319-328.

Pra et al: "Experimental Study on Band Dispersion in Channels Structured with Micropillars" Anal. Chem, 2006, 78, 6519-6525.

Yamada et al: "Size-selective growth of double-walled carbon nanotube forests from engineered iron catalysts" nature nanotechnology, vol. I, Nov. 2006, 131-136.

Malsche et al: "Experimental Study of Porous Silicon Shell Pillars under Retentive Conditions" Anal. Chem. 2008, 80, 5391-5400.

Smet et al: "Influence of the Pillar Shape on the Band Broadening and the Separation Impedance of Perfectly Ordered 2-D Porous Chromatographic Media" Anal. Chem, 2004, 76, 3716-3726.

Gzil et al: "Advantages of Perfectly Ordered 2-D Porous Pillar Arrays over Packed Bed Columns for LC Separations: A Theoretical Analysis" Anal. Chem, 2003, 75, 6244-6250.

Gzil et al: "General Rules for the Optimal External Porosity of LC Supports" Anal Chem, 2004, 76, 6707-6718.

U.S. Appl. No. 12/826,940, Mail Date Aug. 29, 2012, Office Action.

U.S. Appl. No. 13/035,645, Mail Date Sep. 11, 2012, Office Action.

U.S. Appl. No. 13/035,645, Mail Date Oct. 24, 2012, Notice of Allowance.

Shubhodeep Goswami et al: "Aligned Carbon Nanotube Stationary Phases for Electrochromatographic Chip Separations" Chromatographia; An International Journal for Rapid Communication in Chromatography, Electophoresis and Associated Techniques, Vieweg Verlag, WI, vol. 69, No. 5-6, Feb. 3, 2009, pp. 473-480.

Fonverne et al: "In situ Synthesized Carbon Nanotubes as a New Nanostructured Stationary Phase for Microfabricated Liquid Chromatographic Column", Sensors and Actuators B, Elsevier Sequoia S.A., Lausanne, vol. 129, No. 2, Feb. 13, 2008, pp. 510-517.

International Search Report and Written Opinion mailed Sep. 3, 2010 for PCT/US2010/040532.

U.S. Appl. No. 12/826,940, Nov. 30, 2012, Office Action.

U.S. Appl. No. 61/339,095, filed Feb. 26, 2010, Linford et al.

U.S. Appl. No. 61/945,628, filed Feb. 27, 2014, Linford et al.

Sun; "Study on Growth and Mechanism of Single-Walled Carbon Nanotubes on Silicon Substrate", Wanfang Database of Dissertations, dated Jan. 16, 2007; published on Mar. 17, 2008, pp. 1-51; English Absract located on p. 3.

Fang et al.: "Preparation and CO conversion activity of ceria nanotubes by carbon nanotubes templating method", Journal of Rare Earths, vol. 26, No. 2, Apr. 2008, p. 153-157.

Zhang et al.: "Carbon nanotube-assisted synthesis and high catalytic activity of $CeO_2$ hollow nanobeads", Materials Chemistry and Physics, vol. 113 (2009) 527-530.

Zhou, et al.: "Progress in preparation and Applications of Aligned Carbon Nanotubes Arrays", Center for Photon Manufacturing Science, pp. 95-98, May 21, 2007.

Zhun, et al.; "Progress in research on growth mechanism of carbon nanotubes",China Symposium on Active Carbon in 2008; Research Institute of Chemical Defense, Beijing 100083; pp. 181-184; Nov. 1, 2008.

U.S. Appl. No. 60/995,881, filed Sep. 28, 2007, Davis et al.

U.S. Appl. No. 61/270,023, filed Jul. 1, 2009, Linford et al.

U.S. Appl. No. 61/283,281, filed Dec. 2, 2009, Linford et al.

U.S. Appl. No. 12/826,940, Mar. 28, 2013, Office Action.

U.S. Appl. No. 13/035,645, Mar. 25, 2015, Notice of Allowance.

U.S. Appl. No. 12/826,940, Aug. 11, 2015, Notice of Allowance.

* cited by examiner

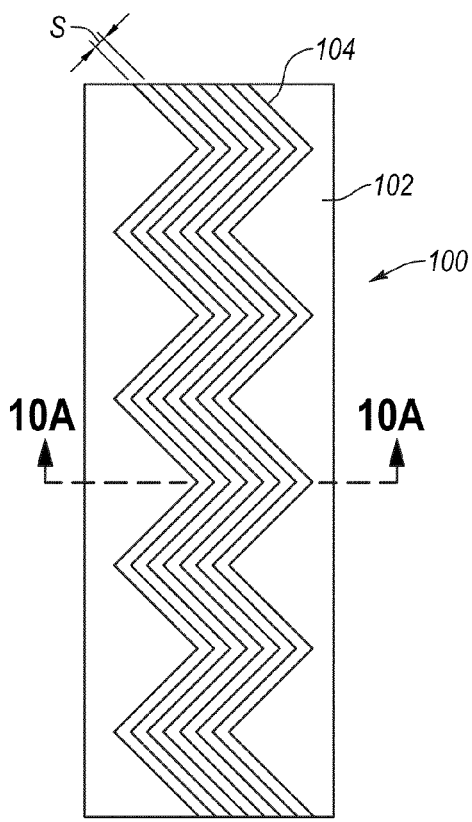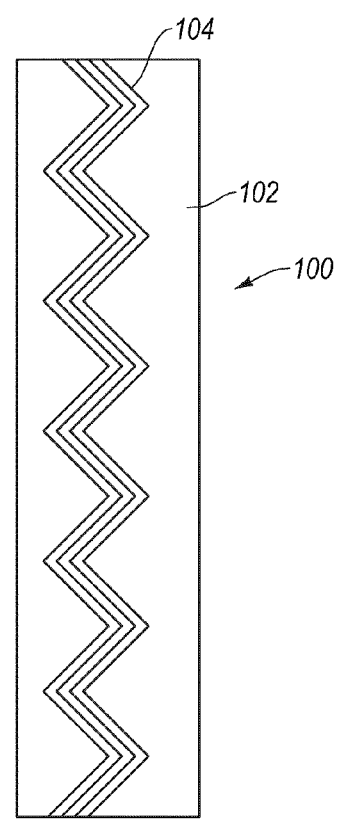
*Fig. 1*      *Fig. 2*
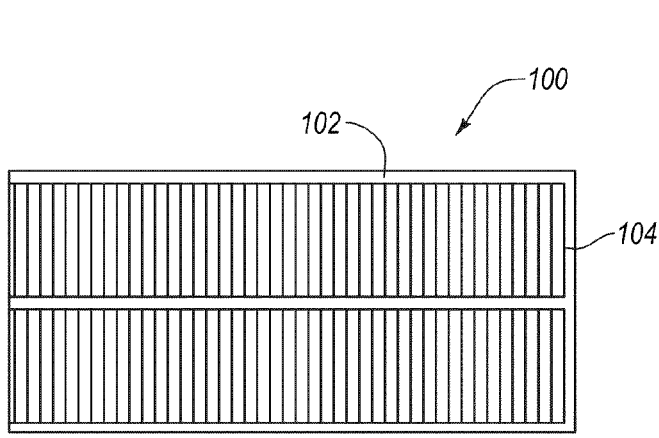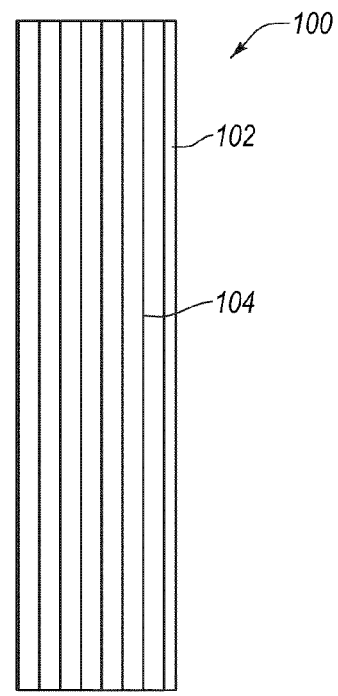
*Fig. 3*      *Fig. 4*

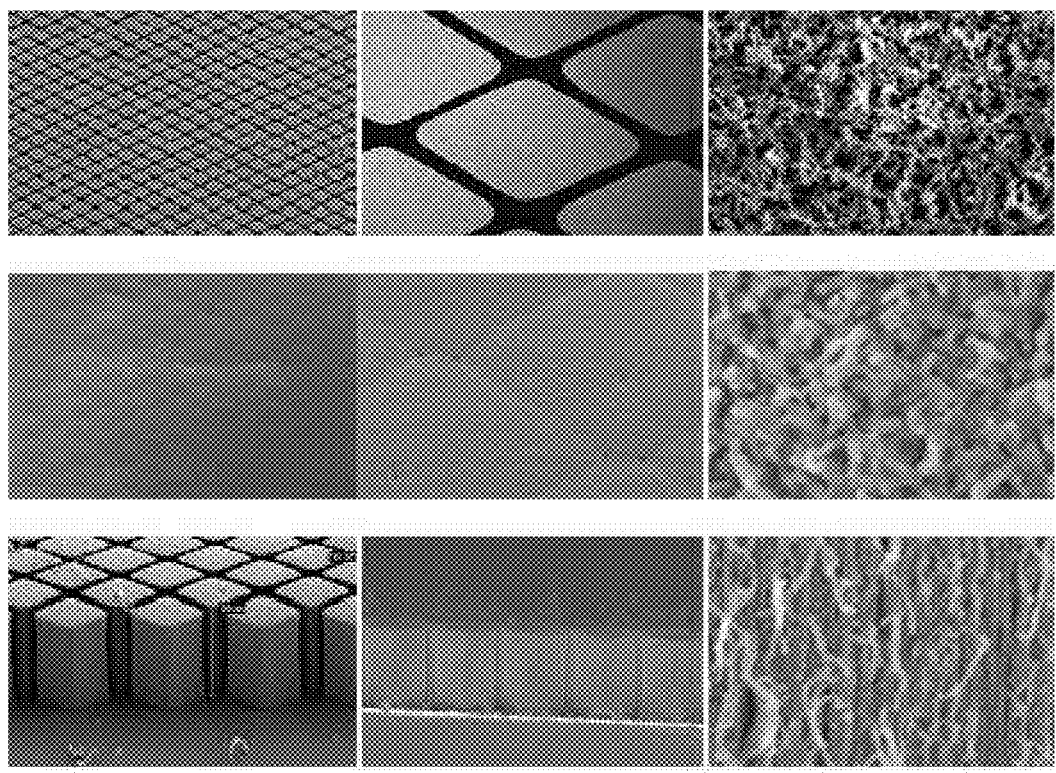
*Fig. 15A*
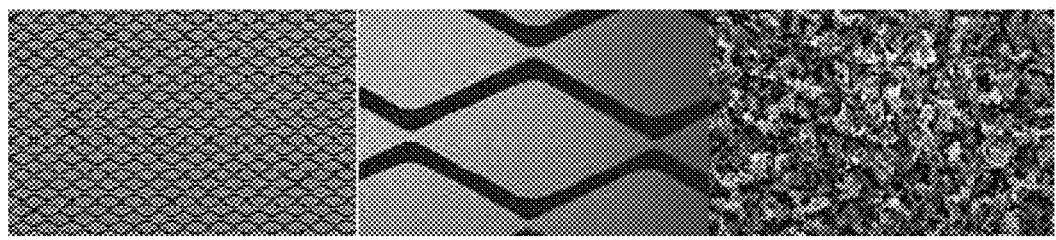
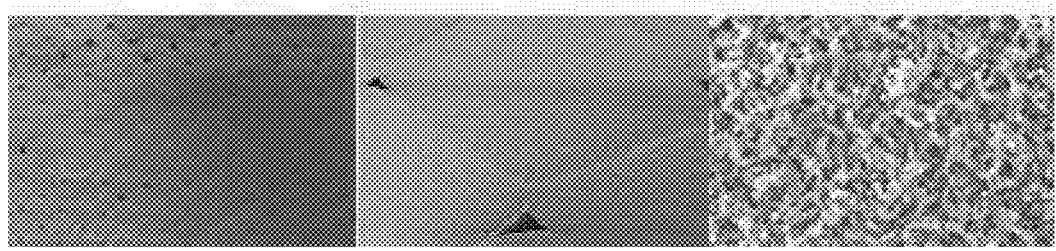
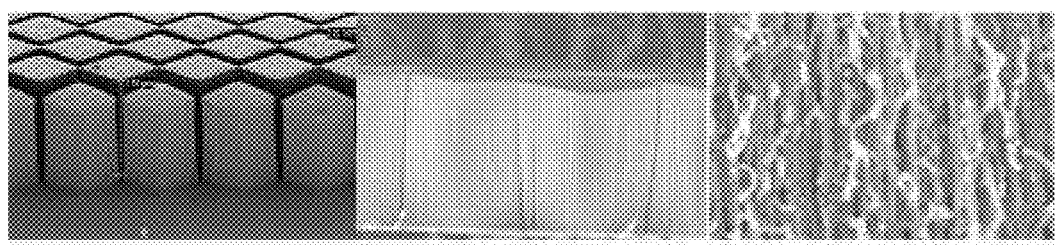
*Fig. 15B*

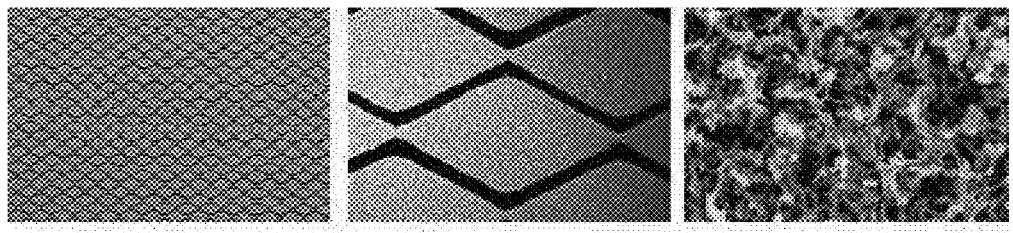
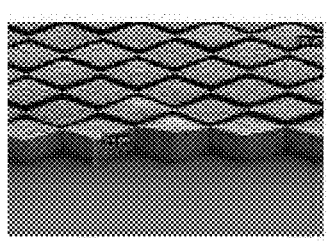
Fig. 15M
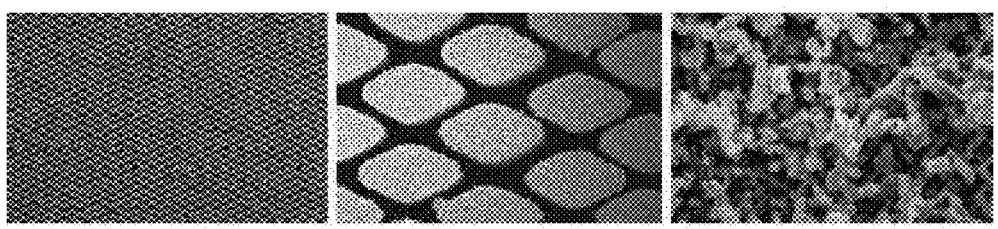
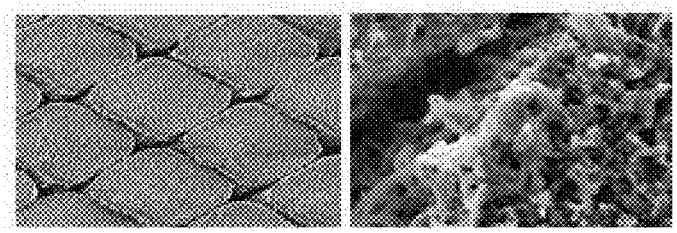
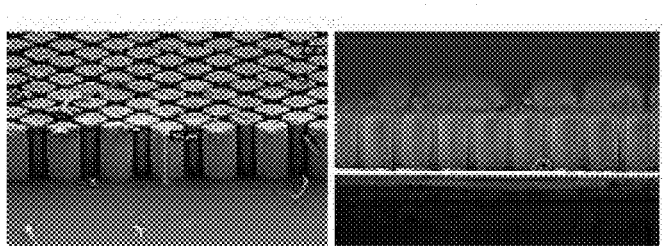
Fig. 15N

THIN LAYER CHROMATOGRAPHY PLATES AND RELATED METHODS

CROSS-REFERENCE TO RELATED APPLICATIONS

This application claims the benefit of U.S. Provisional Application No. 61/283,281 filed on 2 Dec. 2009, entitled "Binder Free Thin Layer Chromatography Plates Assembled Through Carbon Nanotubes." This application is also a continuation-in-part of U.S. application Ser. No. 12/826,940 filed on 30 Jun. 2010, entitled "Thin Layer Chromatography Plates and Related Methods," which claims the benefit of U.S. Provisional Application No. 61/270,023 filed on 1 Jul. 2009, entitled "Binder Free Think Layer Chromatography Plates Assembled Through Carbon Nanotubes." Each of the foregoing patent applications is hereby incorporated herein, in its entirety, by this reference.

BACKGROUND

Chromatography and solid-phase extraction ("SPE") are commonly-used separation techniques employed in a variety of analytical chemistry and biochemistry environments. Chromatography and SPE are often used for separation, extraction, and analysis of various constituents, or fractions, of a sample of interest. Chromatography and SPE may also be used for the preparation, purification, concentration, and clean-up of samples.

Chromatography and SPE relate to any of a variety of techniques used to separate complex mixtures based on differential affinities of components of a sample carried by a mobile phase with which the sample flows, and a stationary phase through which the sample passes. Typically, chromatography and SPE involve the use of a stationary phase that includes an adsorbent packed into a cartridge, column, or disposed as a thin layer on a plate. Thin-layer chromatography ("TLC") employs a stationary phase that is spread in a thin layer on a carrier or substrate plate. A commonly-used stationary phase includes a silica-gel-based sorbent material.

Mobile phases are often solvent-based liquids, although gas chromatography typically employs a gaseous mobile phase. Liquid mobile phases may vary significantly in their compositions depending on various characteristics of the sample being analyzed and on the various components sought to be extracted and/or analyzed in the sample. For example, liquid mobile phases may vary significantly in pH and solvent properties. Additionally, liquid mobile phases may vary in their compositions depending on the characteristics of the stationary phase that is being employed. Often, several different mobile phases are employed during a given chromatography or SPE procedure.

A typical TLC plate is prepared by mixing an adsorbent (which acts as the stationary phase) with a small amount of an inert binder and water. The mixture may be spread as a relatively viscous slurry onto a carrier sheet. The resulting plate can then be dried and activated in an oven. The resulting stationary phase is bound in place to the carrier sheet or other substrate by the binder. The presence of the binder can lead to secondary interactions with the mobile phase, as well as a decrease in separation efficiency.

SUMMARY

Embodiments of the present invention are directed to TLC plates, methods of using such TLC plates in chromatography, and related methods of manufacture in which a plurality of elongated stationary phase structures are formed and affixed to a substrate without the use of a separate binder. The elimination of the use of any binder may prevent unwanted secondary interactions, as well as may improve separation efficiency.

In an embodiment, a method for manufacturing a TLC plate is disclosed. The method includes forming a layer of elongated nanostructures, and at least partially coating the elongated nanostructures with a coating. The coating includes a stationary phase and/or a precursor of a stationary phase for use in chromatography. In an embodiment, the elongated nanostructures may subsequently be removed by heating in an oxidizing environment so as to burn off the elongated nanostructures. In an embodiment, the layer of elongated nanostructures includes a first portion grown on a first portion of the catalyst layer and at least a second portion grown on at least a second portion of the catalyst layer each of which exhibits a selected non-linear configuration.

In an embodiment, a TLC plate is disclosed. The TLC plate includes a substrate, and a plurality of stationary phase structures that extend longitudinally away from the substrate. At least a portion of the plurality of stationary phase structures exhibits an elongated geometry and are substantially free of carbon nanotubes ("CNTs") used as templates for forming the stationary phase structures thereon. In an embodiment, the plurality of stationary phase structures is arranged on the substrate in a selected pattern. A first and at least a second portion of the plurality of stationary phase structures may each be arranged in a non-linear pattern, such as a zigzag pattern or other selected non-linear pattern. Such a non-linear pattern provides increased mechanical stability to the stationary phase structures, as the individual stationary phase structures tend to at least partially intertwine or contact one another, providing support relative to each other. In addition, use of zigzag or other non-linear pattern has been found to counteract a tendency of the material to delaminate from the substrate during oxidation to form the stationary phase structures.

In an embodiment, a method of performing chromatography is disclosed. The method includes providing a TLC plate including a substrate, and a plurality of stationary phase structures extending longitudinally away from the substrate. At least a portion of the plurality of stationary phase structures exhibits an elongated geometry. The method further includes applying a sample to be analyzed to the plurality of stationary phase structures of the TLC plate, and drawing a mobile phase through the plurality of stationary phase structures having the sample applied thereto. The different components of the sample may be separated as the mobile phase and the sample interact with the TLC plate.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

FIG. 1 is a schematic top plan view of an embodiment of a TLC plate intermediate structure including a substrate and a catalyst layer disposed over the substrate, with the catalyst layer exhibiting a zigzag pattern;

FIG. 2 is a schematic top plan view of another embodiment of a TLC plate intermediate structure similar to FIG. 1, but the catalyst layer exhibits an alternative zigzag pattern;

FIG. 3 is a schematic top plan view of another embodiment of a TLC plate intermediate structure similar to FIG. 1, but the catalyst layer exhibits a substantially parallel spacing pattern;

FIG. 4 is a schematic top plan view of another embodiment of a TLC plate intermediate structure similar to FIG. 3, but the catalyst layer exhibits another substantially parallel spacing pattern;

FIG. 10CC is a close-up top plan view of one of the coated CNTs of FIG. 10C.

FIG. 10DD is a close-up top plan view similar to FIG. 10CC, but once the CNTs have been burned off;

DETAILED DESCRIPTION

I. Introduction

Figure 5:
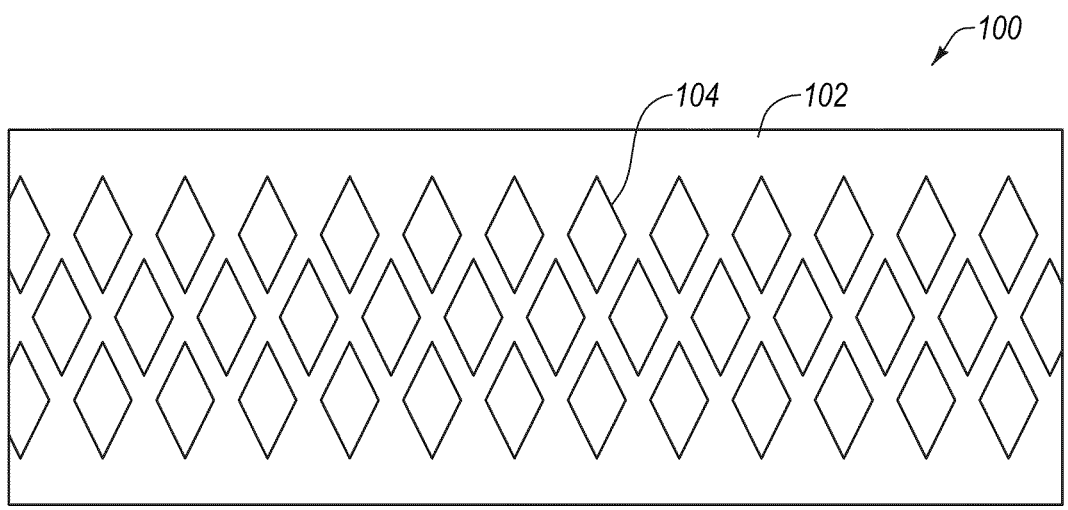
FIG. 5 is a schematic top plan view of another embodiment of a TLC plate intermediate structure similar to FIG. 1, but the catalyst layer exhibits a diamond-shaped pattern.

Embodiments of the present invention are directed to TLC plates and related methods of manufacture and use. The disclosed TLC plates may include a plurality of elongated stationary phase structures affixed to a substrate without the use of a separate binder to provide a highly porous structure suitable for chromatography applications. The elimination of the use of any binder may prevent unwanted secondary interactions, as well as may improve separation efficiency.

II. Embodiments of Methods for Manufacturing TLC Plates and TLC Plate Embodiments In various embodiments, a TLC plate may be manufactured by forming a layer of elongated nanostructures on a substrate and then at least partially coating the elongated nanostructures with a coating that comprises a stationary phase and/or a precursor to the stationary phase for use in chromatography. While the description hereinbelow uses CNTs as an example of a suitable elongated nanostructure, other elongated nanostructures may be used, such as semiconductor nanowires with or without a porous coating, metallic nanowires with or without a porous coating, nanopillars formed by nanoimprint lithography, combinations of the foregoing, or any other suitable nanostructure.

The CNTs may generally be vertically aligned relative to one another, although some contact and/or at least partially intertwining of adjacent CNTs may occur, which may provide increased mechanical stability to the overall CNT forest. The CNTs are coated with a stationary phase that has a thickness less than the CNT spacing, which results in a porous medium through which separation by means of chromatography may occur. The CNT forest is used as a framework on which the stationary phase may be coated and/or formed, resulting in a finished structure that is generally free of any binder for binding the stationary phase to the substrate.

The substrate may include a base, a backing layer disposed on the base, and a catalyst layer disposed on the backing layer that is used to catalyze growth of CNTs over the substrate. Generally, the catalyst layer may be deposited onto the backing layer by any suitable technique. For example, placement of the catalyst layer may be accomplished using a photolithography process, such as masking the catalyst layer and etching to remove regions of the catalyst layer exposed through the mask. Such photolithography processes may be used to produce a catalyst layer having a selected non-linear (e.g., zigzag) pattern. Other patterning processes such as shadow masking with a stencil during catalyst deposition or printing may also be used. In another embodiment, the catalyst layer may be applied so as to coat substantially the entire substrate.

The catalyst layer may comprise any suitable material that catalyzes growth of CNTs under suitable growing conditions (e.g., heating and exposure to a process gas such as $H_2$ and a carbon containing gas such as $C_2H_4$). Various transition metals may be suitable for use as a catalyst layer. Suitable metals include, but are not limited to, iron, nickel, copper, cobalt, alloys of the forgoing metals, and combinations thereof.

The backing layer of the substrate provides support for the structures of the TLC plate. For example, the backing layer provides a support on which the catalyst layer may be deposited, and may also function as a diffusion barrier to help prevent a chemical reaction between the catalyst layer and the base. Examples of backing layer materials may include, but are not limited to, silica (e.g., fused silica), alumina, a low-expansion high-temperature borosilicate glass (e.g., Pyrex 7740 and/or Schott Borofloat glass), steel (e.g., stainless steel), a silicon wafer, a nickel substrate, or any other high-temperature glass or other suitable material. In embodiments where the backing layer comprises a material other than alumina, the backing layer may be prepared for CNT growth by application of a thin layer of alumina over the non-alumina backing layer. The alumina layer may have a thickness between about 5 nm and about 100 nm, more specifically between about 10 nm and about 50 nm, and most specifically between about 20 nm and about 40 nm (e.g., about 30 nm).

A catalyst layer (e.g., iron) may be applied over the backing layer. The catalyst layer may have a thickness between about 0.1 nm and about 15 nm, more particularly between about 0.5 nm and about 8 nm, and even more particularly between about 0.5 nm and about 5 nm (e.g., about 2 to about 3 nm). For example, the catalyst layer may have a thickness of about 0.5 nm, about 1 nm, about 2 nm, about 3 nm, about 4 nm, about 5 nm, about 6 nm, about 7 nm, about 8 nm, about 9 nm, about 10 nm, about 11 nm, about 12 nm, about 13 nm, about 14 nm, or about 15 nm. Although specific catalyst layer thicknesses are disclosed above, the inventors have further found that varying the thickness of the catalyst layer affects some or each of the diameter, density, and height of CNTs grown under otherwise identical conditions. As such, according to an embodiment, the catalyst layer thickness may be altered to change one or more of diameter, density, or height of the grown CNTs.

Figure 6:
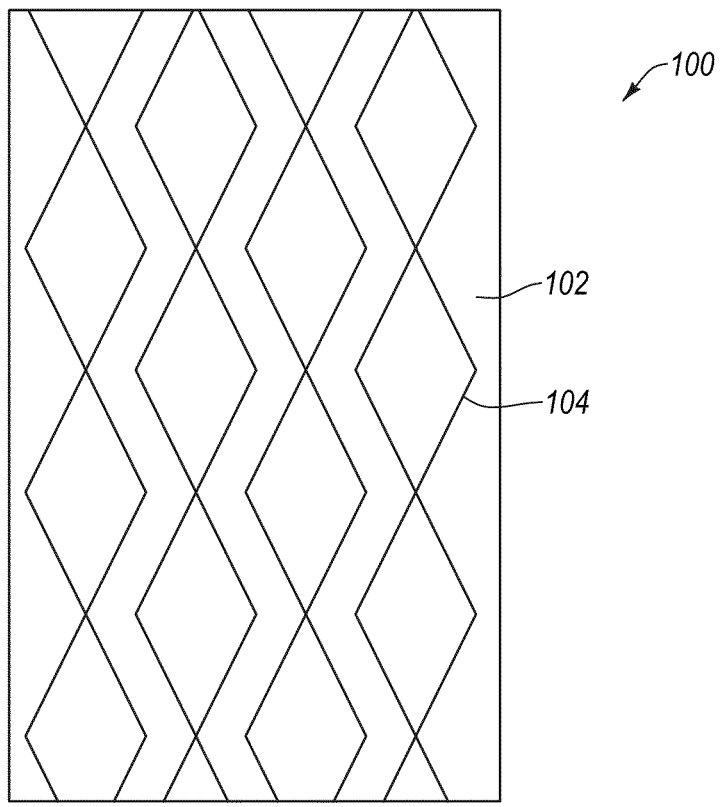
FIG. 6 is a schematic top plan view of another embodiment of a TLC plate intermediate structure similar to FIG. 5, but the catalyst layer exhibits another diamond-shaped pattern.
Figure 7:
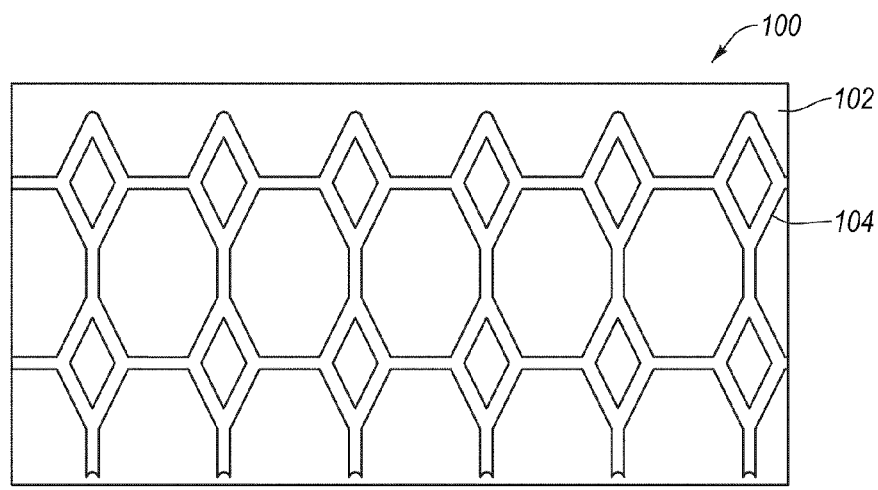
FIG. 7 is a schematic top plan view of another embodiment of a TLC plate intermediate structure similar to FIG. 1, but the catalyst layer exhibits a honeycomb-like pattern.
Figure 8:
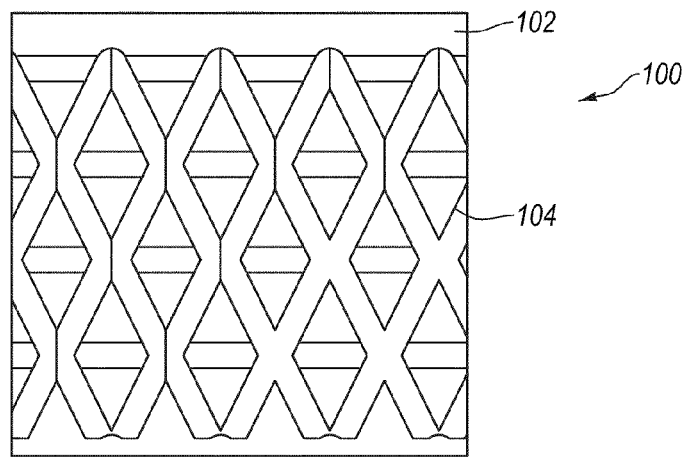
FIG. 8 is a schematic top plan view of another embodiment of a TLC plate intermediate structure similar to FIG. 7, but the catalyst layer exhibits another honeycomb-like pattern.
Figure 9:
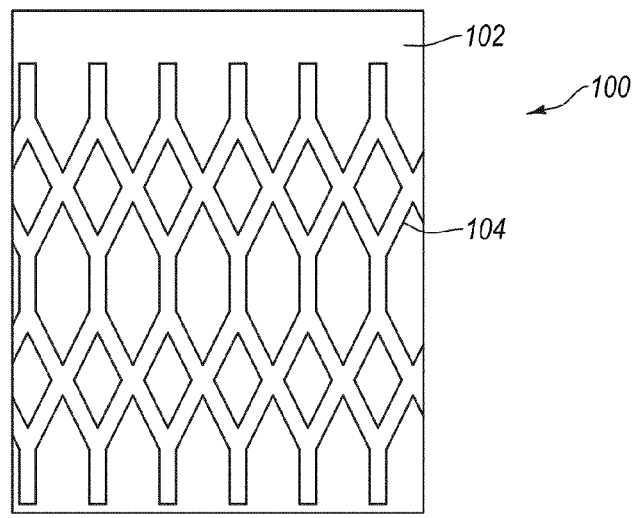
FIG. 9 is a schematic top plan view of another embodiment of a TLC plate intermediate structure similar to FIG. 7, but the catalyst layer exhibits another honeycomb-like pattern.
Figure 10A:
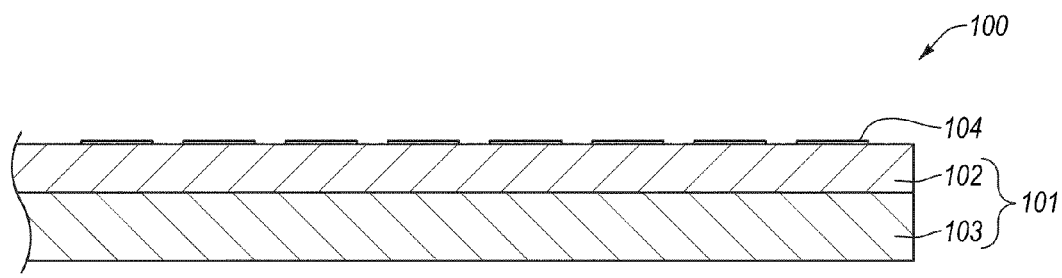
FIG. 10A is a cross-sectional view of the TLC plate intermediate structure of FIG. 1.

The catalyst layer may be applied in a selected non-linear pattern or other pattern, or may be applied over substantially an entire surface of the backing layer. Various embodiments of patterns for the catalyst layer are shown in FIGS. 1-9. For example, FIGS. 1 and 10A show a TLC plate intermediate structure 100 including a substrate 101 having a backing layer 102 disposed on a base 103 and a catalyst layer 104 formed on backing layer 102 in a non-linear zigzag pattern, with the patterned catalyst represented by the dark lines. In some embodiments, periodic breaks may be formed in some or all of the zigzag portions of catalyst layer 104 to provide a more uniform average mobile phase velocity to the TLC plate to be ultimately formed. FIG. 2 illustrates another embodiment of a zigzag pattern for catalyst layer 104, with the patterned catalyst represented by the dark lines. FIGS. 3 and 4 each show a TLC plate intermediate structure 100 including substrate 101 having backing layer 102 disposed on base 103 and catalyst layer 104 formed on backing layer 102 in substantially parallel patterns according to another embodiment, with the patterned catalyst represented by the dark lines. FIGS. 5 and 6 each shows a TLC plate intermediate structure 100 including substrate 101 having backing layer 102 disposed on base 103 and catalyst layer 104 formed on backing layer 102 in various repeating diamond patterns according to various embodiments, with the diamonds representing the catalyst. FIGS. 7-9 each shows a TLC plate intermediate structure 100 including a substrate 101 having backing layer 102 disposed on base 103 and catalyst layer 104 formed on backing layer 102 in different honeycomb-like patterns according to various embodiments. FIGS. 1 and 2 and 5-9 each show a non-linear catalyst pattern, while the patterns of FIGS. 3 and 4 show generally linear catalyst patterns.

The catalyst layer 104 may be patterned to exhibit any desired spacing between adjacent portions of the patterned catalyst layer 104. For example, an average bed spacing "S" is shown in FIG. 1. In an embodiment, an average bed spacing between adjacent portions of patterned catalyst layer 104 is between about 1 μm and about 50 μm, more particularly between about 3 μm and about 20 μm, and most particularly between about 5 μm and about 15 μm (e.g., about 10 μm). One of skill in the art will appreciate that catalyst layer 104 may be formed so as to have any desired pattern and/or spacing "S." In another embodiment, the catalyst layer 104 may be formed so as to cover substantially the entire backing layer 102, lacking any particular distinct pattern. In some embodiments, catalyst layer 104 is spaced inwardly from edges of backing layer 102 in order to substantially prevent growth of CNTs on the edges. In some embodiments, the spacing "S" may vary in one or two directions, such as from zigzag portion to zigzag portion.

With catalyst layer 104 formed on backing layer 102, TLC plate intermediate structure 100 may be placed onto a suitable support (e.g., a quartz support) within a furnace and heated to a temperature within a range of about 600° C. to about 900° C., more particularly between about 650° C. to about 850° C., and even more particularly to between about 700° C. to about 800° C. (e.g., about 750° C.). Prior to CNT growth, the catalyst layer 104 may be annealed in an annealing process in which $H_2$ or another process gas is flowed over the catalyst layer 104 (e.g., within a fused silica tube) while the temperature is increased from ambient temperature to the temperature at which CNT growth will occur. Flow of $H_2$ may be about 300 $cm^3$/min or other suitable flow rate.

A process gas (e.g., $H_2$, ammonia, $N_2$, or combinations thereof) and a carbon-containing gas (e.g., acetylene, ethylene, ethanol, methane, or combinations thereof) are introduced and flowed over the catalyst layer 104. A noble gas (e.g., argon) may also be included with the carbon-containing gas stream to control the rate of growth of CNTs on and over the catalyst layer 104. Flow of the process gas and carbon-containing gas (e.g., ethylene) may be within a ratio of about 0.5:1 to about 1, more particularly between about 0.55:1 and about 0.85:1, and even more particularly between about 0.6:1 and about 0.8:1.

Once the desired height of CNT growth is achieved, flow of the process gas and carbon-containing gas are turned off, and the furnace chamber may be purged with flow of a noble gas (e.g., argon) as the furnace is partially cooled, for example to a temperature between about 100° C. to about 300° C., more particularly between about 150° C. to about 250° C., and even more particularly to between about 175° C. to about 225° C. (e.g., about 200° C.).

In one embodiment, and in order to achieve a higher aspect ratio of base width to CNT height, a "start/stop" method may be employed. For example, the carbon-containing gas may be turned off during CNT growth, causing the CNTs to grow in a myriad of directions. This type of growth may be desired in some embodiments, as it may lead to more mechanically stable CNTs (e.g., such adjacent CNTs may be more likely to contact and/or at least partially intertwine with one another).

Figure 10B:
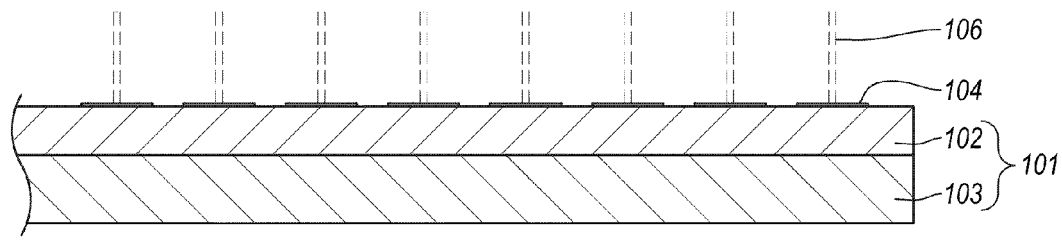
FIG. 10B is a cross-sectional view of the TLC plate intermediate structure of FIG. 10A with CNTs grown on the catalyst layer.

FIG. 10B is a cross-sectional view of an embodiment of a structure similar to that of FIGS. 1 and 10A in which CNTs 106 have been grown on and over catalyst layer 104. CNTs 106 may be grown to extend longitudinally away from the substrate 101. For example, the CNTs may extend substantially perpendicular (i.e., vertical) to respective surfaces of catalyst layer 104 and substrate 101. Grown CNTs 106 may be single walled or multi-walled, as desired. Grown CNTs 106 may have an average diameter between about 3 nm and about 20 nm, more particularly between about 5 nm and about 10 nm (e.g., about 8.5 nm) and an average length of about 10 μm to about 2000 μm, about 10 μm to about 1000 μm, about 10 μm to about 500 μm, about 20 μm to about 400 μm, about 20 µm to about 200 µm, about 100 µm to about 300 µm, about 10 µm to about 100 µm, or about 20 µm to about 200 µm. The grown CNTs 106 may exhibit an average aspect ratio (i.e., ratio of average length to average diameter) of about 10,000 to about 2,000,000, such about 10,000 to about 1,000,000, or about 100,000 to about 750,000.

The average length to which CNTs 106 are grown may be chosen based on the particular chromatography application. For example, the average length of the CNTs 106 may be about 10 µm to about 100 µm for ultra-thin layer chromatography ("UTLC"), the average length of the CNTs 106 may be about 100 µm to about 300 µm for high-performance thin layer chromatography ("HPTLC"), and the average length of the CNTs 106 may be about 500 µm to about 2000 µm for preparative liquid chromatography ("PLC").

Additional details regarding growth of CNTs 106 may be found in U.S. patent application Ser. Nos. 12/239,281 and 12/239,339 entitled X-RAY RADIATION WINDOW WITH CARBON NANOTUBE FRAME. Both of the above applications claim priority to U.S. Provisional Patent Application No. 60/995,881. U.S. patent application Ser. Nos. 12/239,281 and 12/239,339 and U.S. Provisional Patent Application No. 60/995,881 is each incorporated herein, in its entirety, by this reference.

Although CNTs 106 are illustrated as being uniformly spaced, CNTs 106 may be at least partially intertwined with each other to form a vertical wall of CNTs 106. As previously discussed, the at least partial intertwining and/or contact of CNTs 106 with each other helps reduce, limit, or prevent the vertical wall of CNTs 106 from bending out of plane. Furthermore, the rigidity of the wall of CNTs 106 may be further enhanced to reduce, limit, or prevent out of plane bending thereof by patterning catalyst layer 104 in a selected non-linear pattern (e.g., the pattern shown in FIG. 1) and growing respective portions of CNTs 106 on the individual non-linear portions of catalyst layer 104 to form respective walls of CNTs 106.

Figure 10C:
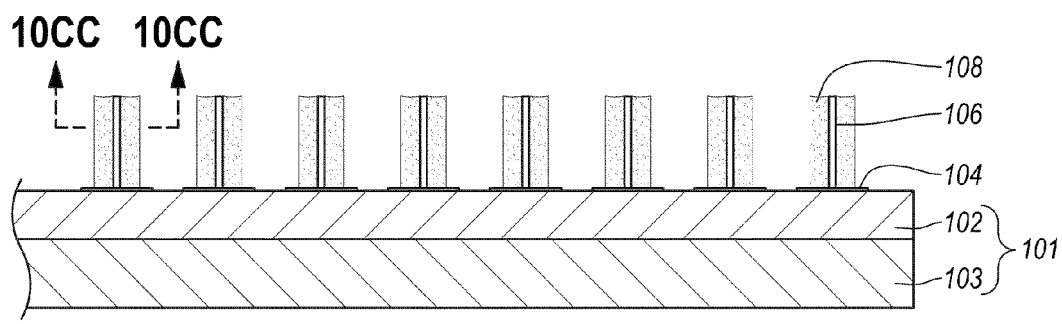
FIG. 10C is a cross-sectional view of the TLC plate intermediate structure of FIG. 10B once the CNTs have been at least partially coated by a coating.
Figure 10C:
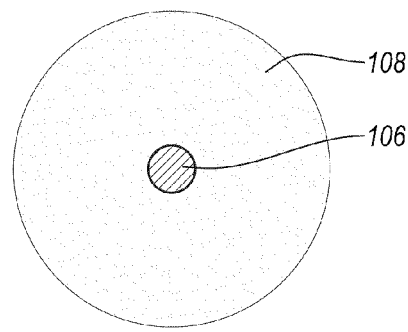

The CNTs are used as a framework to be infiltrated with a material that may increase the mechanical stability of the overall structure and provide a stationary phase for use in chromatography applications. Referring to FIG. 10C, after growth, CNTs 106 may be infiltrated with one or more infiltrants (e.g. a precursor gas) so that a coating 108 deposits on the CNTs 106. Coating 108 comprises a stationary phase and/or a precursor to the stationary phase. Examples of materials for coating 108 include, but are not limited to, elemental silicon (e.g., deposited from a precursor $SiH_4$ gas), silicon dioxide, silicon nitride, elemental aluminum, aluminum oxide, elemental zirconium, zirconium oxide (e.g., zirconium dioxide), elemental titanium, titanium oxide, amorphous carbon, graphitic carbon, and combinations of the foregoing. Because the choice of coating 108 may change the selectivity of the resulting TLC plate, coating 108 used for manufacture of any given TLC plate may be selected depending on the intended use of the TLC plate.

In one embodiment, infiltration of CNTs 106 may be accomplished using chemical vapor deposition (e.g., low pressure chemical vapor deposition ("LPCVD")) or another suitable deposition process (e.g., atomic layer deposition ("ALD")). For example, the TLC plate intermediate structure shown in FIG. 10B may be placed into a furnace and heated to about 500° C. to about 650° C., more particularly between about 540° C. to about 620° C., and even more particularly to between about 560° C. to about 600° C. (e.g., about 580° C.). During infiltration, the infiltration pressure may be maintained at less than about 400 mTorr. For example, the infiltration pressure may be maintained between about 50 mTorr and about 400 mTorr, more particularly between about 100 mTorr to about 300 mTorr, and even more particularly to between about 150 mTorr to about 250 mTorr (e.g., about 200 mTorr). Under such temperature and pressure conditions, the infiltrant flows over CNTs 106 to cause a coating 108 (see FIG. 10C) to form on CNTs 106. The amount of deposition of the coating material achieved may be affected by process time. For example, process time for the infiltration may be between about 0.5 hours and about 10 hours, more particularly between about 1 hours and about 5 hours, and most particularly between about 1 hours and about 4 hours (e.g., about 3 hours).

Amorphous carbon infiltration of the CNTs 106 may be performed using a carbon source flowing through the fused silica tube at elevated temperatures. For example, ethylene may be flowed, for example, at a rate of 170 $cm^3$/min mixed with argon at a flowed rate of 200 $cm^3$/min and at a temperature of about 900° C. Due to the light absorptive characteristics of amorphous carbon, the detection of analytes after separation may require a post sample preparation. This process may include marking the analytes with an oxidation stable marker and removing the carbon in a high temperature oxygen environment (e.g., with an oxygen plasma). For example, the developing agent may comprise silane, either in the gas phase or in solution, which would be applied to the TLC plate. In an oxidative environment (e.g., an oven, a plasma, or flame), the carbon would be burned away leaving a pattern of $SiO_2$ that would reveal where migration of analytes had occurred.

CNTs 106 may be infiltrated with elemental silicon by LPCVD and then oxidized, if needed or desired, to form $SiO_2$. Other deposition processes for $SiO_2$ include direct $SiO_2$ LPCVD, ALD, or by other CVD processes with $SiH_4$ and $O_2$ or $SiH_2Cl_2$ with $N_2O$, or by other methods for CNT infiltration that will be apparent to one of skill in the art in light of the present disclosure. The inventors have performed LPCVD infiltration of CNTs with elemental silicon followed by dry oxidation. The silicon infiltration process employed $SiH_4$ as the source for elemental silicon. The silicon infiltration was done by flowing $SiH_4$ at a rate of about 20 $cm^3$/min at a temperature of about 530° C. with a pressure of about 160 mTorr for about 1-3 hours, depending on film thickness (degree of infiltration) desired. After the silicon deposition, the material was placed into a furnace in air and treated to between about 500° C. and about 1000° C. for between about 1 and about 10 hours. This process converted the elemental silicon to silicon dioxide, while also removing CNTs 106 by oxidizing them into CO and/or $CO_2$ thereby leaving elongated stationary phase structures made from silicon dioxide without any significant amount of CNTs 106 filling. Depending on the extent of the oxidation process, the elongated stationary phase structures may be substantially solid nanowires without a hollow central portion where the CNTs 106 where present. This process produces a white and/or transparent $SiO_2$ material that may be used for chromatography.

ALD processes may alternatively be used to infiltrate CNTs 106 with a conformal coating of a selected material having chromatographic abilities, or which may be subsequently processed to result in such abilities. ALD may be used to infiltrate CNTs with $SiO_2$. One such process may use $SiCl_4$ and water at a selected temperature. $SiCl_4$ is introduced into the chamber containing CNTs 106 and is allowed to react therewith for a predetermined time. After finishing the self-limiting chemisorptions/physisorption process, water is introduced into the chamber which reacts with the bound $SiCl_4$ to produce a conforming layer of $SiO_2$ on CNTs 106. This process is repeated until a predetermined film thickness of $SiO_2$ is achieved. In other embodiments, a process that is ALD-like may be employed to infiltrate CNTs 106. For example, $SiCl_4$ is introduced, but excess $SiCl_4$ may or may not be entirely removed by pumping before water is introduced. In turn, excess water may or may not be entirely removed before $SiCl_4$ is introduced. By not entirely removing excess reagent, as would be appropriate for a true ALD process, faster deposition of $SiO_2$ may be possible. This same strategy of incomplete removal of material could be contemplated for other ALD chemistries that could be used to infiltrate CNTs 106. It is also noted that perfect conformal coating of uniform thickness of CNTs 106 may or may not be desirable. An infiltration process may be designed to produce a rough non-uniform thickness coating so as to increase the surface area of the support.

FIG. 10C is a cross-sectional view of the TLC plate intermediate structure shown in FIG. 10B in which CNTs 106 have been infiltrated with infiltrant so that a coating material deposits onto CNTs 106 to form coating 108 that at least partially coats and extends about a periphery of respective CNTs 106. In the case in which the infiltrant is a silicon precursor gas such as silane, coating 108 may be silicon. However, as discussed above, other precursor gases may be used so that coating 108 may be formed from aluminum or zirconium. Depending on the infiltrant selected, coating 108 may at least partially or substantially coat the entire array of CNTs 106 only, or it may also coat the intervening portions of backing layer 102 and catalyst layer 104 between the CNTs 106, resulting in a TLC plate that is one coherent mass. Coating 108 on respective CNTs 106 shown in FIG. 10C forms respective high aspect ratio structures exhibiting an elongated annular geometry (e.g., a substantially hollow cylinder). CNTs 106 act as templates around which the coating material deposits. In some embodiments, coating 108 may be porous or non-porous. The particular aspect ratio of the elongated structures made from coating 108 depends on the height of the template CNTs 106, the deposition time, the process temperature (e.g., temperature of infiltrant and of CNTs 106), or combinations of the foregoing process parameters. FIG. 10CC is a close-up top plan view of a single coated CNT 106 of FIG. 10C. An average aspect ratio (i.e., ratio of average length to average diameter) of the plurality of elongated structures defined by coating 108 coating respective CNTs 106 may be about 10,000 to about 2,000,000, such about 10,000 to about 1,000,000, or about 100,000 to about 750,000. The average radial thickness of coating 108 coating the CNTs 106 may be about 10 nm to about 100 nm, more particularly about 20 nm to about 80 nm, and even more particularly about 25 nm to about 40 nm (e.g., about 30 nm). The average length of the elongated structures defined by coating 108 may be substantially the same or similar as the template CNTs 106.

In some cases, random growth of CNTs 106 followed by infiltration and optionally oxidation of coating 108 can pose a potential problem. During the oxidation process of converting silicon to silicon dioxide, the material undergoes a volume expansion due to the addition of the oxygen. The volume expansion causes the material to delaminate from the backing, particularly during longer, more complete oxidation times. One way to reduce, minimize, or eliminate such delamination from the backing is by (e.g., zigzag or other non-linear) patterning the CNT growth catalyst, which places voids into the overall structure allowing for volume expansion during the oxidation step. In addition, patterning of the stationary phase medium on the micron-scale may improve separation efficiency. SEM images show how varying the thickness of the catalyst layer causes different heights of CNT growth. Such SEM images are shown in FIGS. 14A-14P.

Figure 14A:
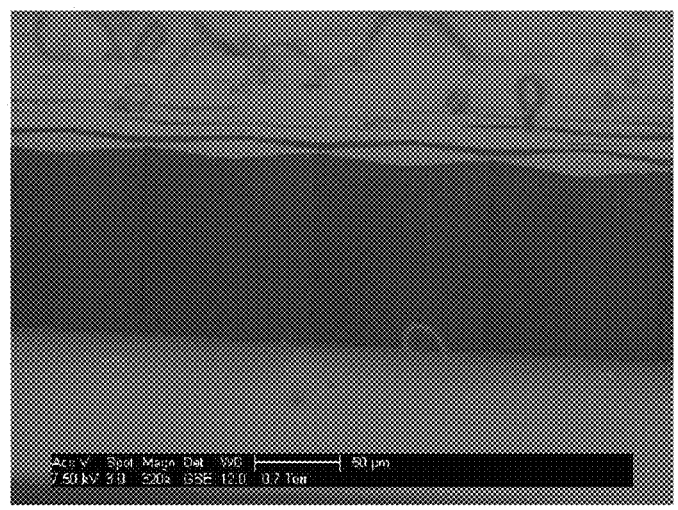
FIGS. 14A-14P show SEM images of TLC plates having different catalyst layer thicknesses and CNTs and $SiO_2$ elongated nanostructures formed thereon with different corresponding heights.
Figure 14B:
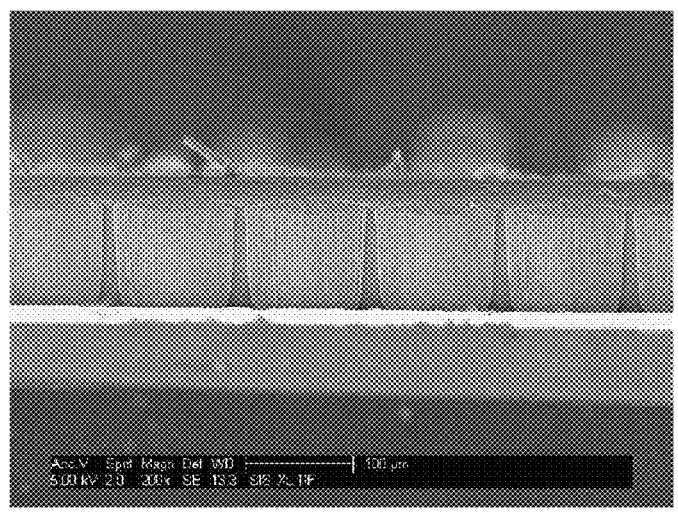
Figure 14C:
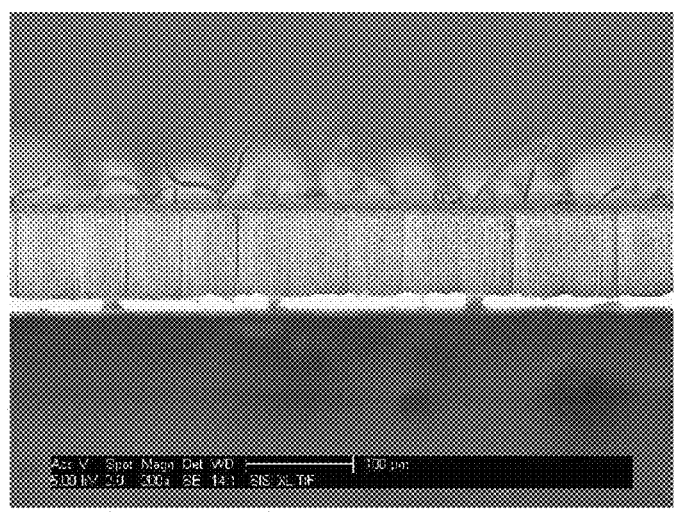
Figure 14D:
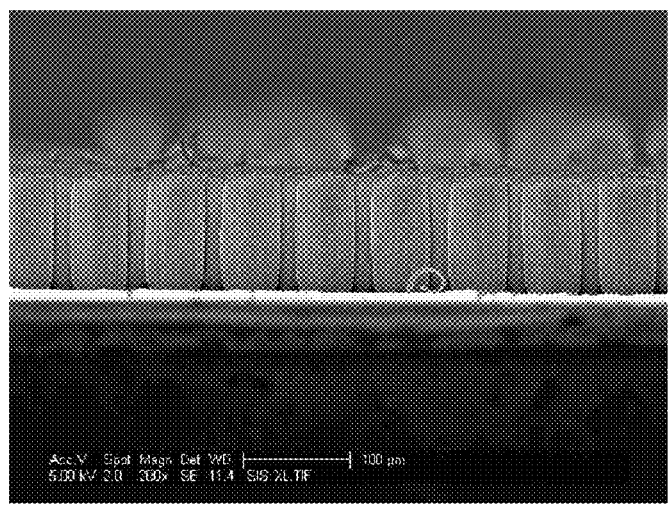
Figure 14E:
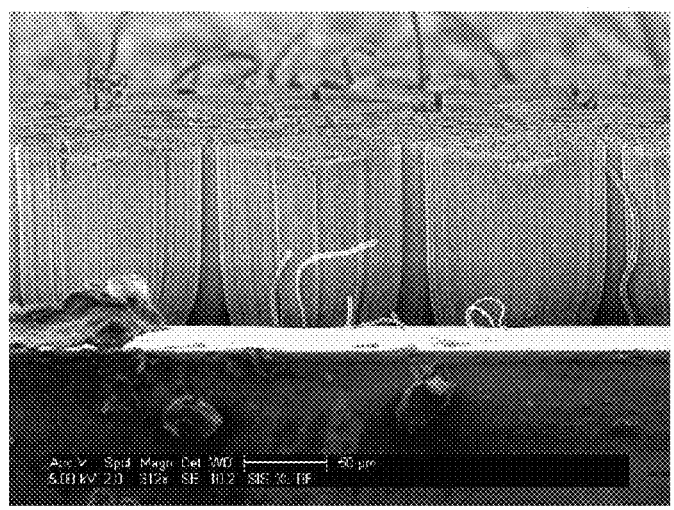
Figure 14F:
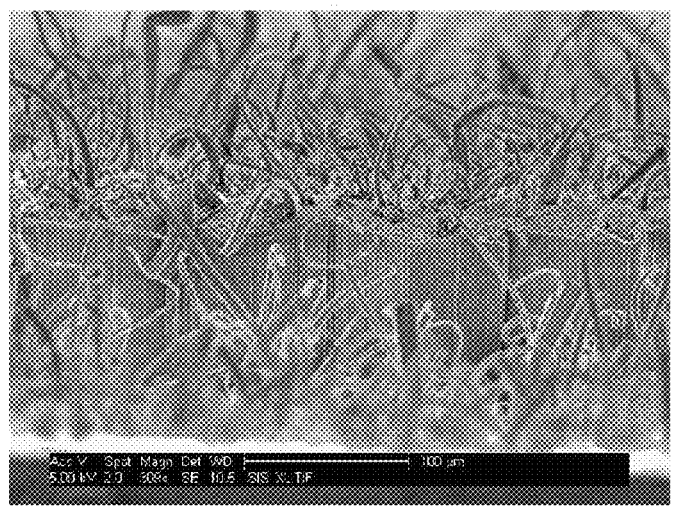
Figure 14G:
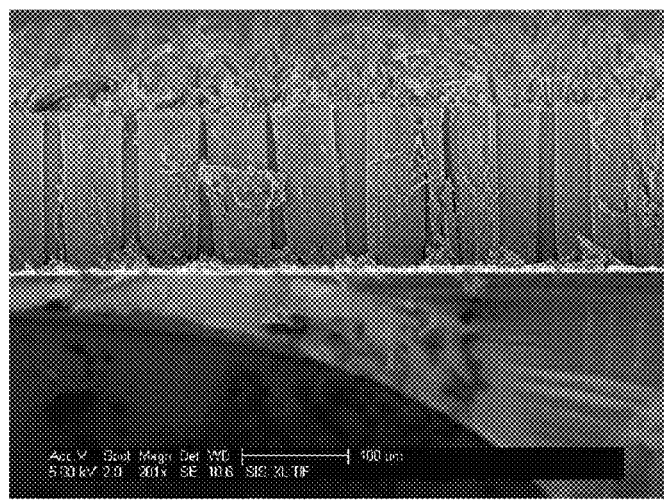
Figure 14H:
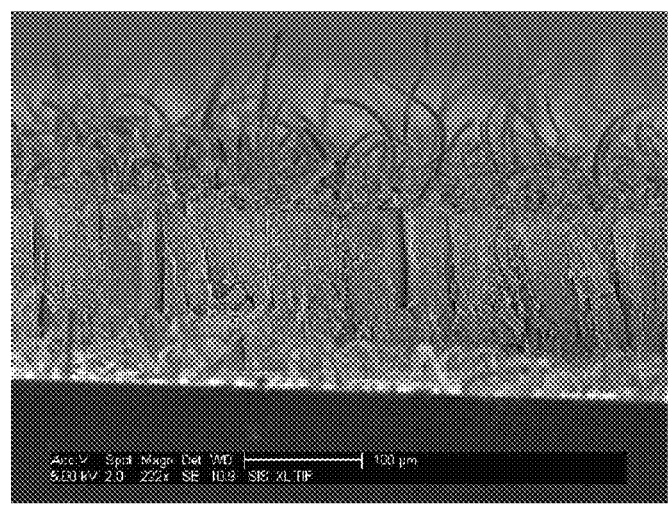
Figure 14I:
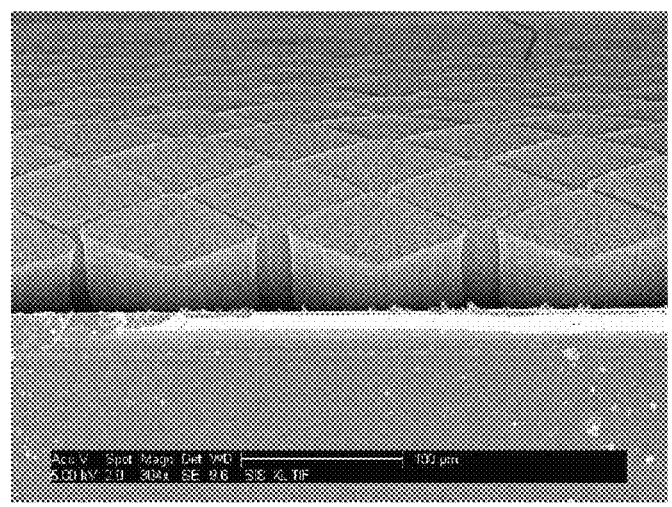
Figure 14J:
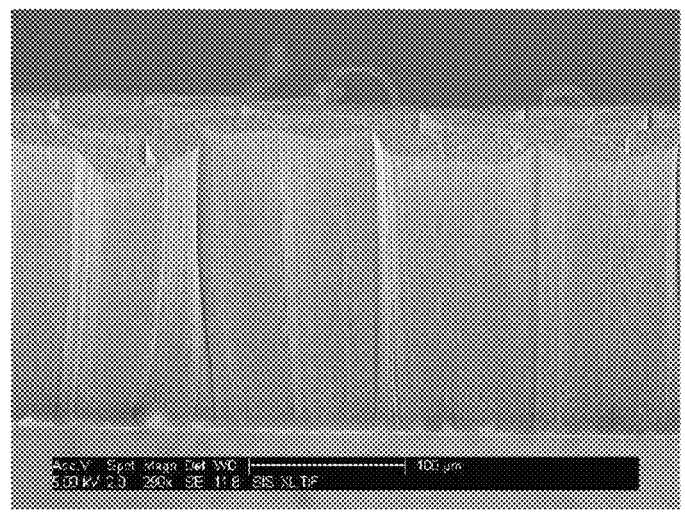
Figure 14K:
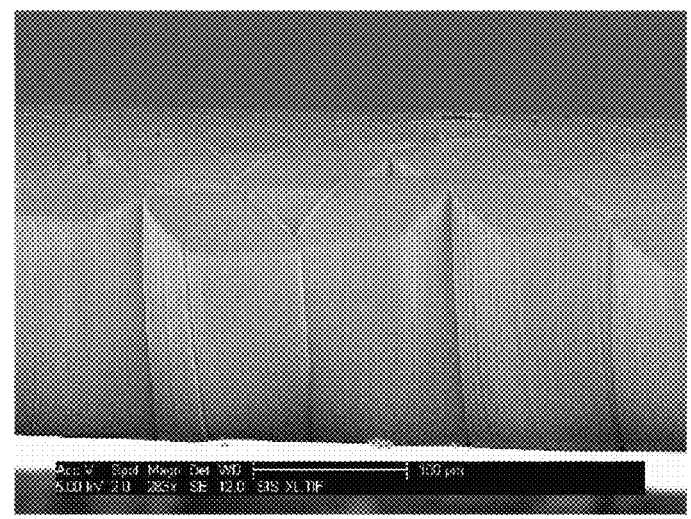
Figure 14L:
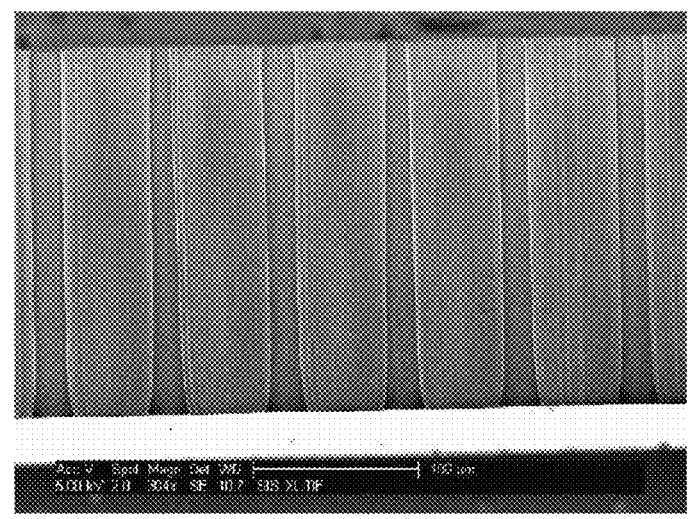
Figure 14M:
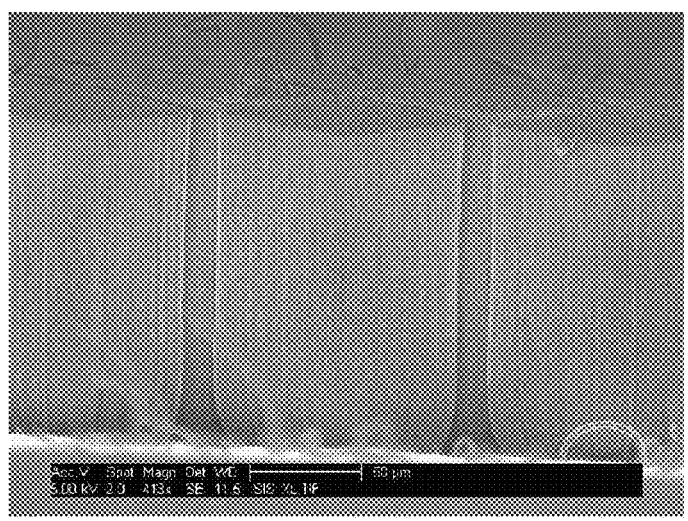
Figure 14N:
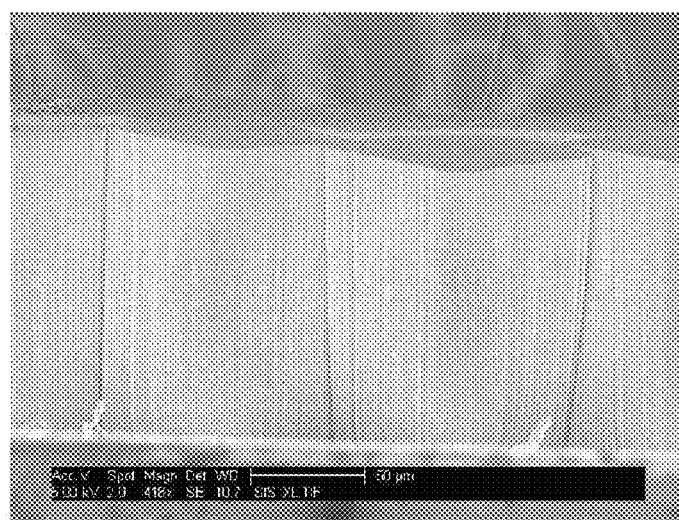
Figure 14O:
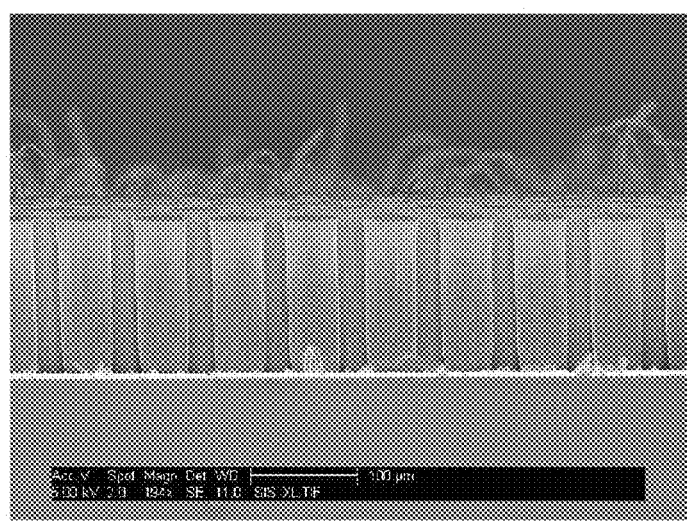
Figure 14P:
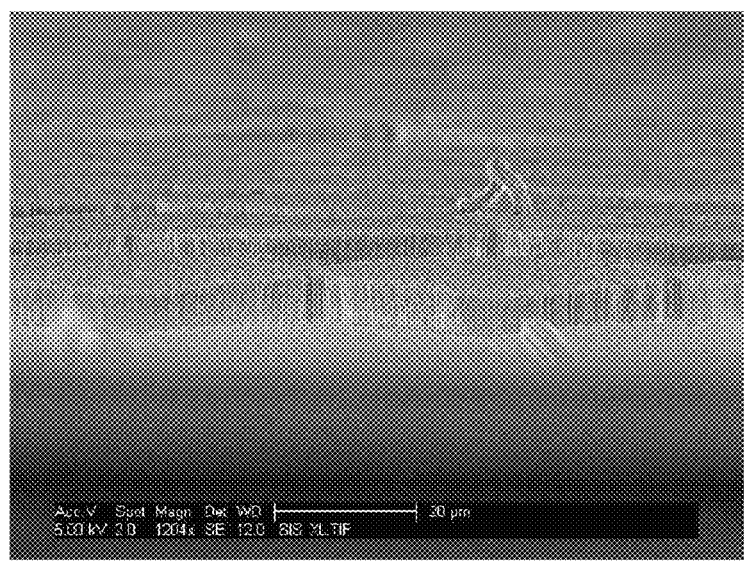

FIGS. 14A-14P show the appearance of the infiltrated plates after the oxidation step where silicon is converted to silicon dioxide and CNTs 106 are removed. It is noted that the change in color is indicative of a change in the material (i.e., the CNTs are dark, the $SiO_2$ is light). SEM images of the patterned media before and after oxidation show a volume expansion during oxidation (see FIGS. 15A-15O).

As described above, an average bed spacing between adjacent portions of patterned catalyst layer 104 may be between about 1 µm and about 50 µm, more particularly between about 3 µm and about 20 µm, and most particularly between about 5 µm and about 15 µm (e.g., about 10 µm). The growth of CNTs 106 followed by infiltration with infiltrant and/or growth of coating 108 around CNTs 106 results in less spacing between adjacent elongated structures defined by coating 108 as they grow laterally outward and towards one another. For example, an average spacing between adjacent elongated structures defined by coating 108 may be between about 0.5 µm and about 30 µm, more particularly between about 2 µm and about 10 µm, and most particularly between about 4 µm and about 8 µm. Such spacing results in a bulk structure having very high bulk porosity (i.e., the spacing between adjacent structures act as pores through which the mobile phase and sample carried therewith advance as a result of capillary action. When present, porosity of any individual coating 108 (i.e., as opposed to bulk porosity resulting from spacing between adjacent structures) may also contribute to the overall porosity TLC plate.

In an embodiment, CNTs 106 may be partially or substantially completely removed once the coating 108 has been deposited onto CNTs 106. For example, the TLC plate intermediate structure shown in FIG. 10C may be placed into a furnace and heated (e.g., to about 800° C. to about 900° C., or about 850° C.) in the presence of an oxidizing atmosphere (e.g., an oxygen atmosphere) so as to remove (e.g., burn off) substantially all of CNTs 106, leaving only coating 108 disposed on the backing layer 102 and catalyst layer 104 of TLC plate substrate 101. Such an oxidation step may also serve to convert coating 108 into the stationary phase by oxidizing the as-deposited coating 108 if it is not already a stationary phase. For example, if coating 108 is silicon, aluminum, or zirconium, it may be oxidized to silicon oxide, aluminum oxide, or zirconium oxide, respectively. An embodiment of a method for removal of the CNTs 106 may include oxidizing coating 108 using an oxygen plasma. Other methods for at least partially removing CNTs 106 may include dissolution of CNTs 106, or removal by any method.

Figure 10D:
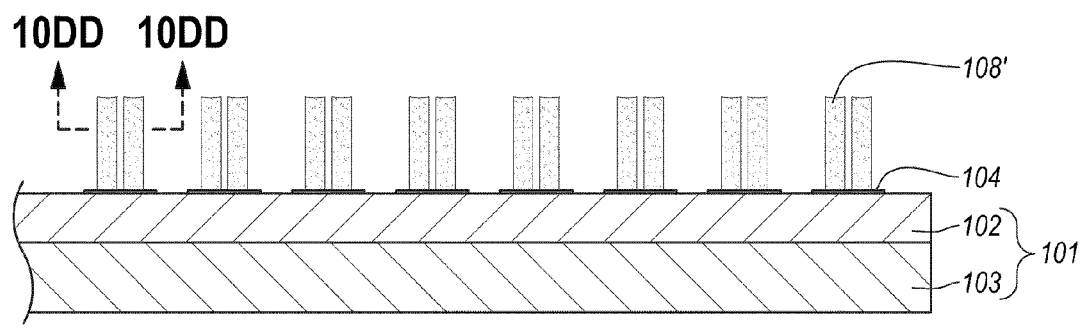
FIG. 10D is a cross-sectional view of the TLC plate intermediate structure of FIG. 10C once the CNTs have been burned off, oxidizing the coating so as to form stationary phase structures.
Figure 10D:
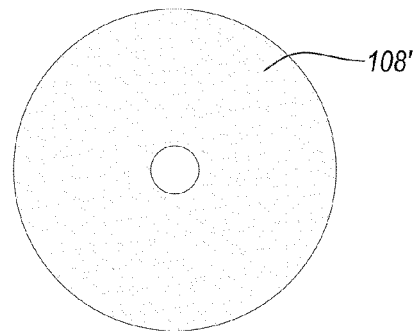

FIG. 10D is a cross-sectional view of the structure shown in FIG. 10C in which the CNTs 106 have been removed and coating 108 has been oxidized to form a plurality of elongated stationary phase structures 108'. FIG. 10DD is a top plan view of stationary phase structures 108' once CNTs 106 have been burned off. FIG. 10D clearly shows the overall high aspect ratio configuration of the stationary phase structures 108'. The dimensions of the plurality of elongated stationary phase structures 108' may be substantially the same or similar dimensions as the plurality of elongated structures defined by coating 108 prior to oxidation. The oxidation process may occur for at least about 5 hours, more particularly at least about 10 hours, and most particularly for at least about 24 hours. The inventors have found that increased oxidation increases the separation efficiency achieved by the oxidized stationary phase. In some embodiments, only a portion of the coating 108 coating respective CNTs 106 is oxidized. In other embodiments, substantially all of the coating 108 coating respective CNTs 106 is oxidized.

Although, the elongated stationary phase structures 108' are illustrated in FIGS. 10D and 10DD as being hollow after removal of the CNTs 106, depending on the extent of oxidation process, the elongated stationary phase structures 108' may be substantially solid nanowires in which the space previously occupied by the CNTs 106 is consumed or filled by the oxide. In embodiments in which the coating 108 is deposited by ALD or an ALD-like process (e.g., ALD deposition of silicon oxide), the resultant elongated stationary phase structures may be hollow elongated cylinders, with the hollow being where a CNT 106 was located.

Removal of CNTs 106 before use of the TLC plate may prevent CNTs 106 from interfering (e.g., through a secondary interaction) with separation of a mobile phase during use of the TLC plate. In addition, it results in a white and/or transparent stationary phase; thereby making evaluation of the chromatography results easier than if the stationary phase is black or brown. In embodiments in which the coating 108 comprises amorphous carbon, the CNTs 106 may not be removed, as both the coating 108 and CNTs 106 comprise carbon, thereby substantially eliminating the possibility of a secondary interaction as a result of the CNTs 106 being present in the stationary phase formed during infiltration.

In some embodiments, the stationary phase structures 108' comprises a material that is white, off white, transparent, or generally light in color so that the compounds of the mobile phase separated during use of the TLC plate are visible on the surface of the TLC plate after being developed. Silicon and/or silicon dioxide are examples of materials that provide such a color contrast. In some embodiments, a fluorescent material (e.g., ZnS) may be incorporated in the TLC plate. For example, the fluorescent material may at least partially coat and/or may be incorporated in the stationary phase structures 108', may at least partially coat intervening portions of backing layer 102 between the stationary phase structures 108', or both.

After oxidation and removal of CNTs 106, in some embodiments, the TLC plate so formed may be placed in a furnace in the presence of HCl so that HCl vapors result in placement of hydroxyl groups onto the surface of stationary phase structures 108' to functionalize stationary phase structures 108'. Additional chemical functionality and selectivity may be added to the stationary phase structures 108' by, for example, silanolization with alkyl moieties through any suitable gas phase chemistry. When the stationary phase structures 108' comprise silica (e.g., by oxidizing a silicon coating 108), the silica may be functionalized by bonding $C_8$ chains, $C_{18}$ chains, $NH_2$, or combinations thereof to the silica.

In an embodiment, the stationary phase may be exposed to water vapor after the oxidation step and during cooling from the oxidation temperature to ambient temperature. Acidified water vapor may be employed to hydroxylate the surface. For example, this may be done by placing the TLC plate above a boiling HCl solution so that the vapors of the solution are allowed to interact with the stationary phase. The boiling solution may include methanol to aid in surface wetting. Other components that may be used include other strong acids (e.g., nitric acid, HBr), organic acids (e.g., acetic acid, formic acid, trifluoroacetic acid) or other suitable chemical that can hydroxylate the surface. In one embodiment, exposure may be about 5 minutes, although shorter or longer times may be employed. The silanol containing surfaces may be silanized using a wide variety of silanes (e.g., mono-chlorosilanes, di-chlorosilanes, tri-chlorosilanes, or combinations thereof). Examples of suitable silanes include alkyl silanes (e.g., octadecyl trichlorosilane, octadecyldimethylchlorosilane, perfluoro alkyl silanes), amino silanes, phenyl silanes, cyano silanes, biphenyl silanes, or combinations thereof. Such silanes may be monofunctional (e.g., including one Si—Cl group, one Si—$OCH_3$ group, one Si—$OCH_2CH_3$ group, or one Si—$OC(O)CH_3$ group), or silanes bearing more than one surface reactive functional group. Molecules such as octadecyldiisopropylchlorosilane are contemplated, where the isopropyl groups impart added hydrolytic stability to the silica TLC plate.

Exposure to acidified water vapor may result in an improvement in the chromatographic performance of the material. FIGS. 16A-16D demonstrate how using such an acid treatment influences the chromatographic capabilities of the material. The chemical species separated in the image in FIGS. 16A-16D are Rhodamine 6G, Sunset Yellow FCF, and Sufurhodamine B. Rhodamine 6G is retained to the greatest degree on the TLC plate.

In an embodiment, the TLC plates may be produced with a concentration zone. This involves having an area that has relatively low retention where compounds may be spotted. This allows for the mobile phase to quickly pull the analyte through this area and then the analytes will slow down when they reach the normal sorbent bed. This can be done by making the pre-concentration area with a low density of the stationary phase structures and/or selectively functionalizing this area with a chemical species that allows for reduced retention of analytes.

In some embodiments, substrate 101 may be scribed or partially cut before or after growth of CNTs 106 and/or coating CNTs 106. By scribing or cutting substrate 101, smaller TLC plates may be fabricated by breaking a larger TLC plate along a scribe/cut line of substrate 101.

Figure 11A:
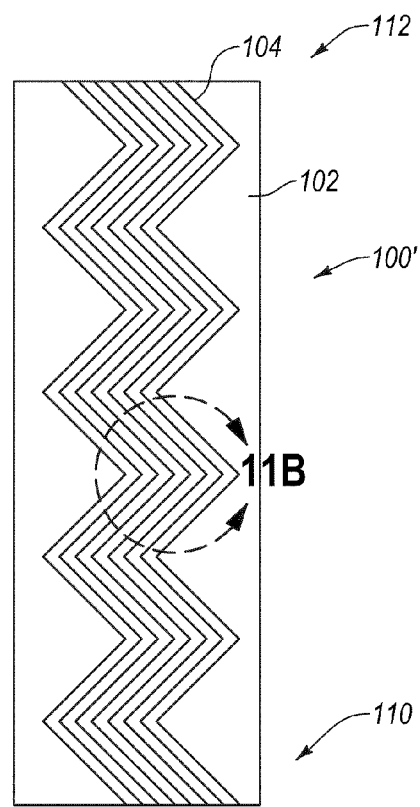
FIG. 11A is a schematic top plan view of a TLC plate manufactured from a TLC plate intermediate structure similar to that of FIG. 1.
Figure 11B:
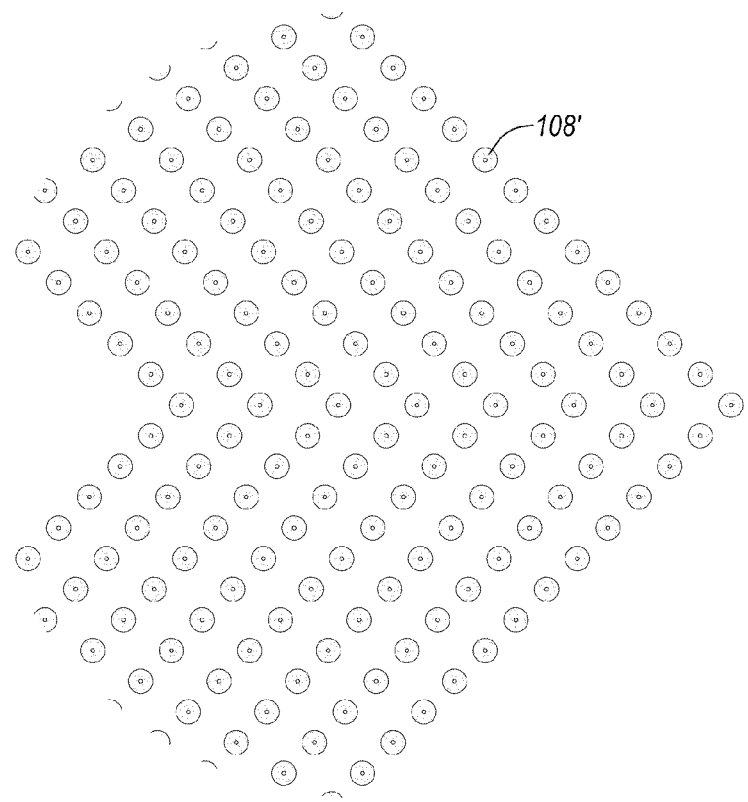
FIG. 11B is a close-up top plan view of the TLC plate intermediate structure of FIG. 11A showing several of the high aspect ratio deposited stationary phase structures disposed on the TLC plate substrate.

FIG. 11A is a top plan view of an embodiment of a TLC plate 100'. FIG. 11B is a close-up view of a portion of TLC plate 100' includes stationary phase structures 108' that are arranged between an end 110 and an end 112 of TLC plate 100'. TLC plates prepared according to the inventive methods disclosed herein provide a stationary phase in which the stationary phase is affixed to the substrate of the TLC plate without the use of any separate binding agent (e.g., typically calcium sulfate). Such binding agents can interfere with the performance of the TLC plate as the result of secondary interactions resulting from the binding agent. The elimination of the need for any binding agent results in a more high efficiency TLC plate while minimizing and/or preventing such secondary interactions.

The spacing of the stationary phase structures 108' is illustrated in FIGS. 11A and 11B as being generally uniform. However, in some embodiments, the density of the stationary phase structures 108' may be different (e.g., greater or less) in different locations of the TLC plate 100'. For example, the density of the stationary phase structures 108' may be different (e.g., greater or less) near end 110 than near end 112. As an alternative to or in addition to the density of the stationary phase structures 108' varying with location, the composition of the stationary phase structures 108' may vary with location. As a non-limiting example, one portion of the stationary phase structures 108' may comprise zirconium oxide and another portion of the stationary phase structures 108' may comprise silica.

Furthermore, TLC plates prepared according to the inventive methods disclosed herein provide a stationary phase having a particularly high porosity. The high porosity, as well as the absence of a binder may result in increased efficiency of the TLC plate during use in analyzing a sample within a mobile phase. In one embodiment, the TLC plates formed according to the disclosed methods are used to analyze a sample material. In one embodiment, the sample to be analyzed is applied to the stationary phase structures 108' of TLC plate 100' (e.g., near end 110). A mobile phase solvent or solvent mixture is then drawn along TLC plate 100' (e.g., upwardly) by capillary action (e.g., by placing TLC plate 100' in a container including the solvent or solvent mixture). As the solvent or solvent mixture is drawn along the TLC plate 100' via capillary action toward opposite end 112, the sample is dissolved in the mobile phase and separation of components within the sample is achieved because different components of the sample ascend the TLC plate 100' at different rates. The high aspect ratio stationary phase structures 108' as well as the bulk porosity as a result of the spacing between individual high aspect ratio stationary phase structures 108' results in excellent separation efficiency of components within the sample as the sample components are carried through the stationary phase structures 108' by the mobile phase (e.g., a solvent or solvent mixture). The TLC plates 100' may also be used in HPTLC in which one or more of the method of use steps may be automated so as to increase the resolution achieved and to allow more accurate quantization.

III. Working Examples

The following working examples are for illustrative purposes only and are not meant to be limiting with regards to the scope of the specification or the appended claims.

Example 1

Individual TLC plates were formed by applying a 30 nm alumina layer over a backing layer. A 2-3 nm film of iron catalyst was deposited on the alumina layer and patterned by photolithographic process to form a TLC plate intermediate structure. The TLC plate intermediate structure was placed in a quartz support tube in a furnace and heated to about 750° C. while flowing about 500 standard $cm^3$/min of $H_2$ process gas through the quartz tube. Once the furnace reached about 750° C., a flow of carbon-containing $C_2H_4$ gas was initiated at a flow of about 700 standard $cm^3$/min. After growth of the CNTs were accomplished, the flow of $H_2$ and $C_2H_4$ gases were turned off, and the quartz tube was purged with argon at a flow of about 350 standard $cm^3$/min while the furnace cooled to about 200° C. The grown CNTs had a diameter of about 8.5 nm.

The grown CNTs were coated with silicon using LPCVD to deposit undoped polycrystalline silicon. The CNTs were placed in an LPCVD furnace and heated to about 580° C. at a pressure of about 200 mTorr while flowing about 20 standard $cm^3$/min of $SiH_4$ for approximately 3 hours. The LPCVD process coated both the CNTs and the alumina layer. After coating with silicon, the coated TLC plate intermediate structure was placed into a furnace and heated to about 850° C. and held at that temperature while being exposed to the atmosphere, resulting in removal of the CNTs, as well as oxidation of the deposited silicon to silicon dioxide. Different oxidation samples were prepared in which oxidation was conducted for about 5 hours, about 10 hours, and about 24 hours. Testing showed that an increased oxidation time increases the ability of an analyte of the mobile phase to migrate through the silicon/silicon dioxide stationary phase.

Figure 12A:
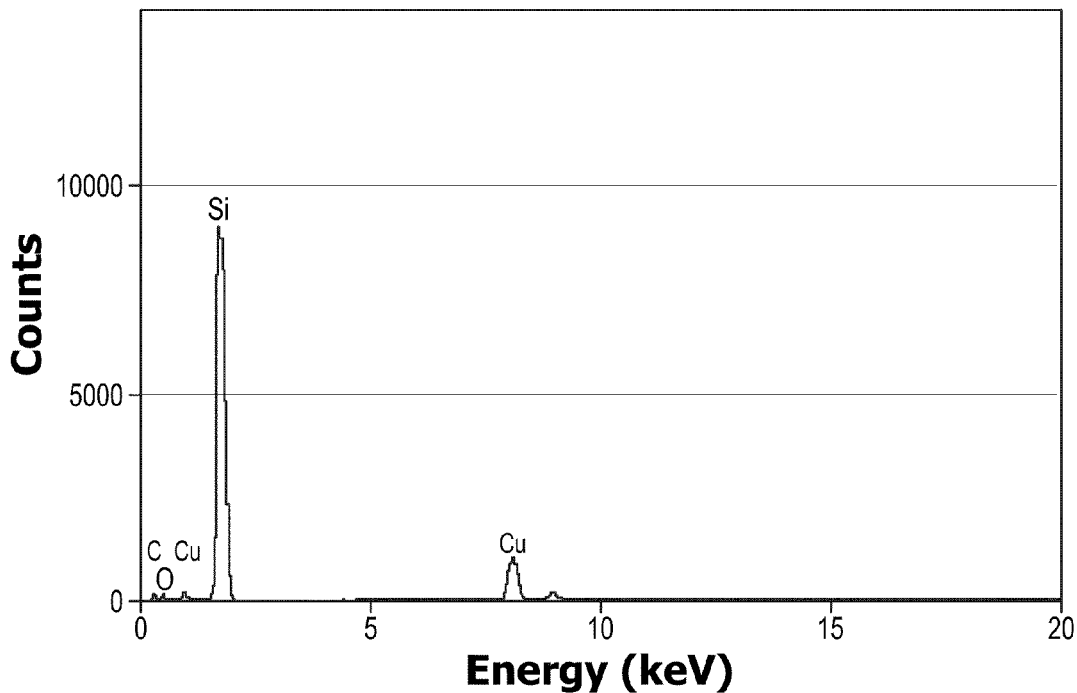
FIGS. 12A and 12B show graphs illustrating energy dispersive x-ray spectroscopy ("EDX") spectra of a TLC plate before and after oxidation according to working examples of the invention.
Figure 12B:
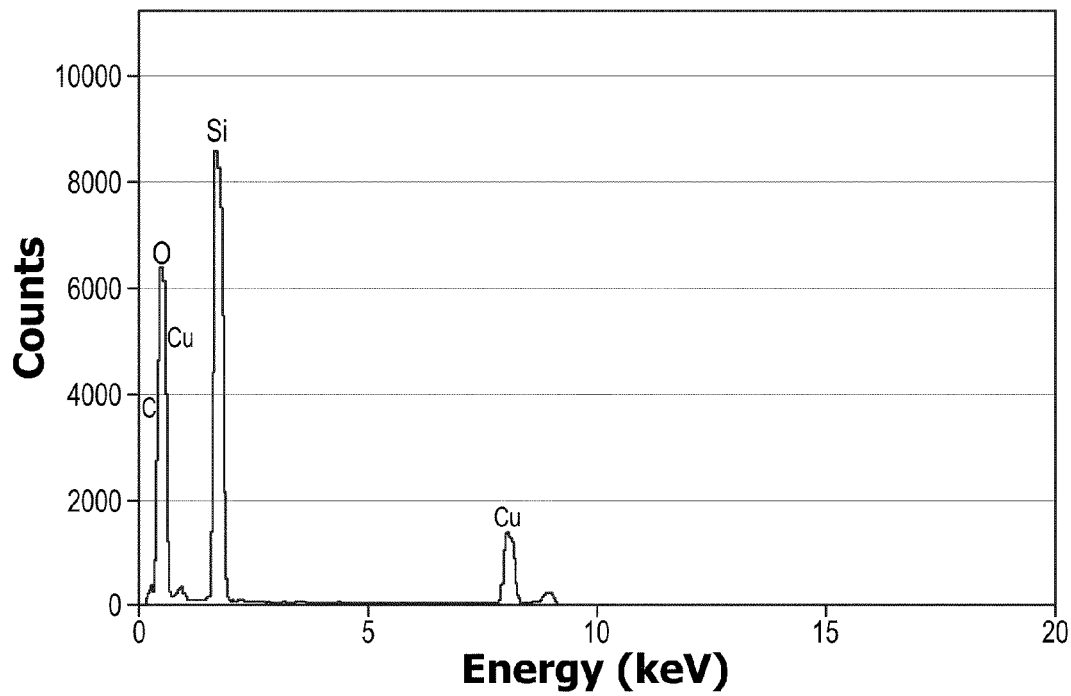
Figure 13A:
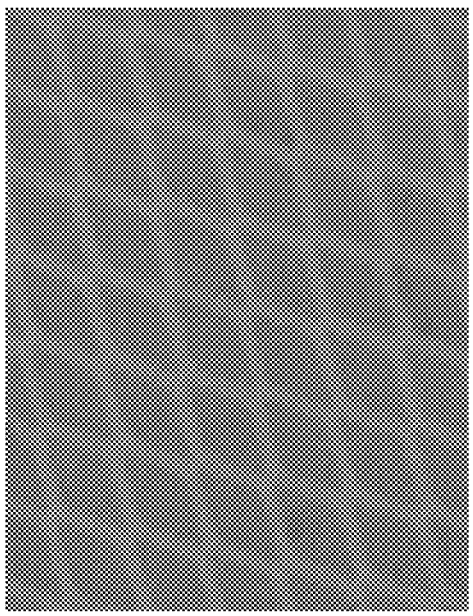
FIGS. 13A-13D show scanning electron microscopy ("SEM") images of various non-linear catalyst layer patterns formed over an alumina substrate.
Figure 13B:
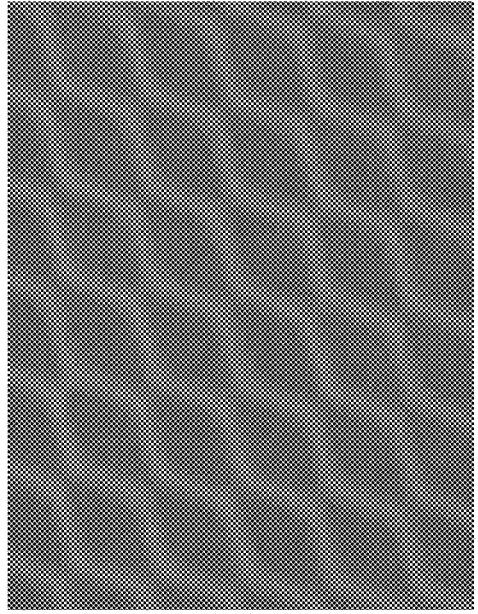
Figure 13C:
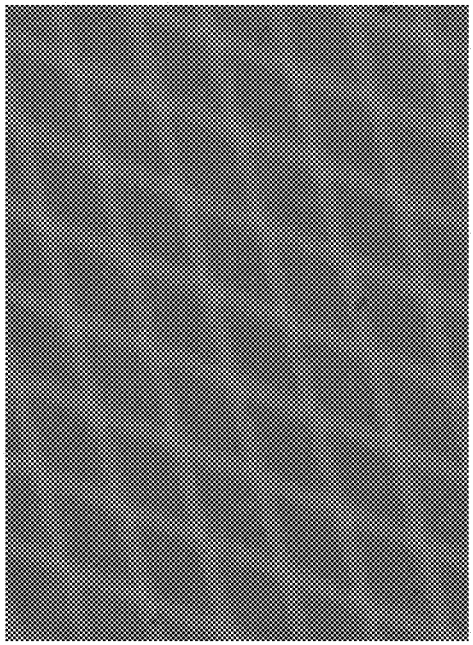
Figure 13D:
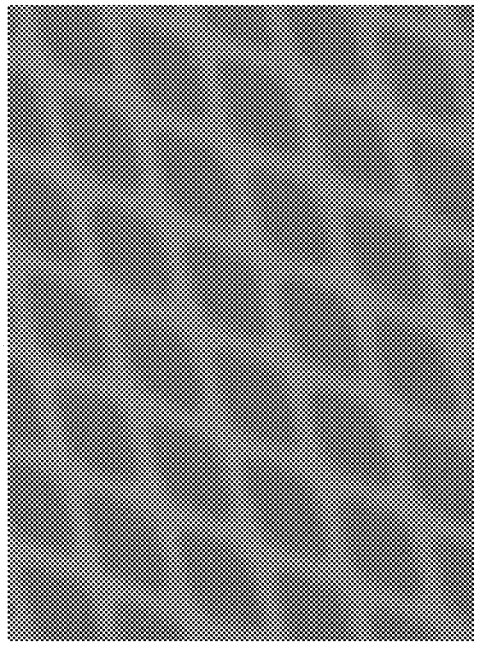

FIGS. 12A and 12B show EDX spectra of the plate before and after oxidation. Before oxidation, carbon is present. After oxidation, minimal carbon remains. Moreover, oxygen is chemically grafted onto the surface of the silicon, forming silicon dioxide.

Examples 2 Through 35

Individual TLC plates were formed by applying a 30 nm alumina layer over a substrate. Afterwards, a photoresist was applied, further followed by photolithography and development. After development, the alumina layer and the photoresist was then coated with a predetermined amount of catalyst material. In these examples, a 2, 4, 6, or 7 nm layer of iron was deposited on top of the photoresist and the alumina layer. After deposition of the iron catalyst, the substrate was placed into a solvent acetone bath used to lift off the remaining resist and the iron on it, as seen in FIGS. 13A-13D. The TLC plate intermediate structures were then used for CNT growth by annealing the catalyst material by flowing 300 $cm^3$/min of $H_2$ through a 1 inch fused silica tube while the furnace was heated from ambient temperature to a temperature between 650° C. and 850° C. After annealing, the CNTs were grown by flowing 100 to 1000 $cm^3$/min ethylene mixed with 300 $cm^3$/min $H_2$ through the fused silica tube. Afterwards, the furnace was cooled while the fused silica tube was purged with 380 $cm^3$/min argon to remove any remaining ethylene and hydrogen.

Figure 17:
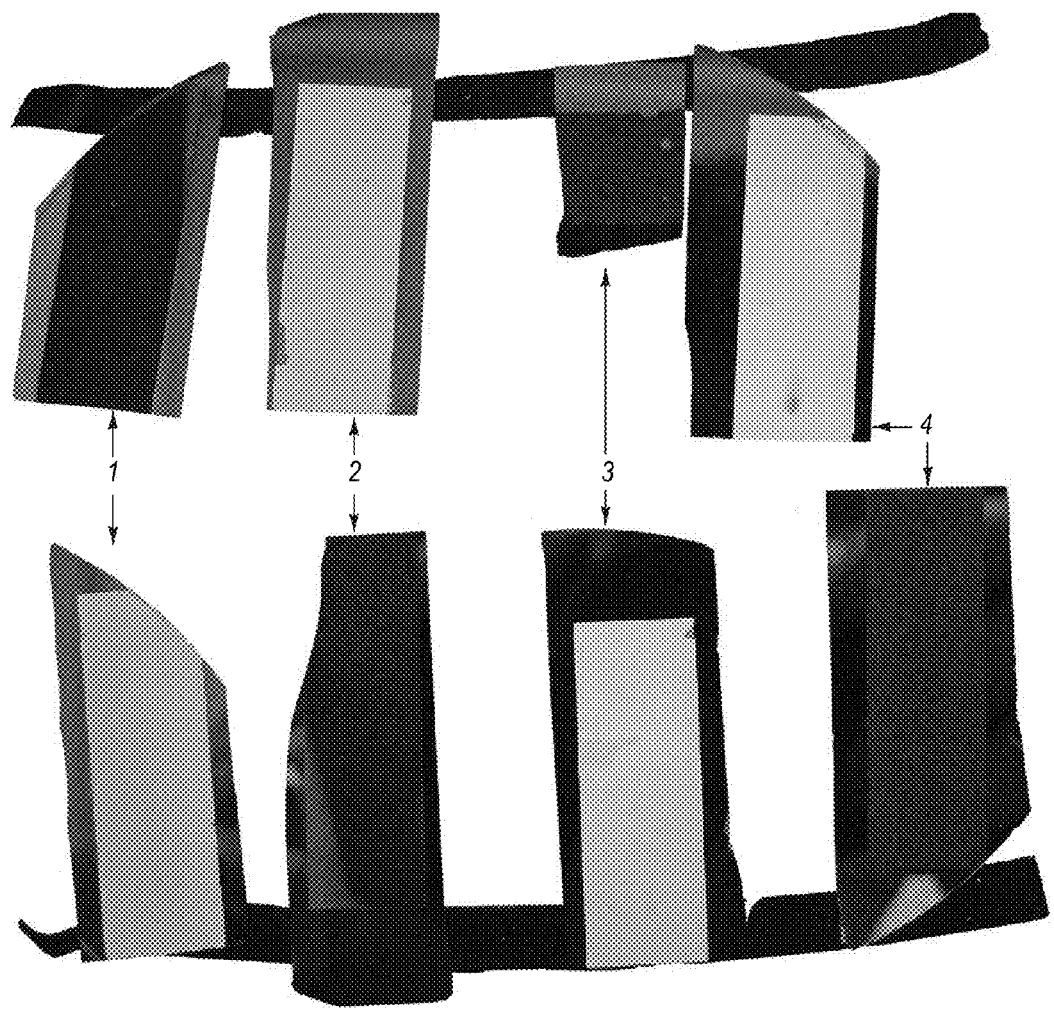
FIG. 17 shows an image of various silicon infiltrated CNT structures as well as the same structures after oxidation.

The CNTs were then infiltrated with elemental silicon by LPCVD and then oxidized to $SiO_2$. The infiltration process used 20 $cm^3$/min $SiH_4$ at 530° C. with a pressure of 160 mTorr for about 1 hour. After the silicon infiltration, the material was placed into a furnace in air and heated to between 500° C. and 1000° C. for between 1 and 10 hours to convert the elemental silicon to silicon dioxide and also remove the CNTs. This process produced a white, $SiO_2$ material suitable for use in chromatography applications. FIG. 17 illustrates oxidized and non-oxidized examples of silicon infiltrated CNT TLC trays so-formed. The silicon infiltrated CNTs are brownish (darker) in color, while the white plates are the oxidized TLC plates. FIGS. 14A-14P show additional SEM images of these examples. Table I below provides information relative to each of these prepared Examples.

TABLE I

| Example | FIGURE | Fe Thickness | Height of $SiO_2$ Nanostructures |
|---|---|---|---|
| 2 | 14A | 7 nm | 105 μm |
| 3 | 14B | 7 nm | 90 μm |
| 4 | 14C | 7 nm | 80 μm |
| 5 | 14D | 7 nm | 100 μm |
| 6 | 14E | 6 nm | 100 μm |
| 7 | 14F | 6 nm | 130 μm |
| 8 | 14G | 6 nm | 140 μm |
| 9 | 14H | 6 nm | 130 μm |
| 10 | 14I | 4 nm | Warped plate (height not determined) |
| 11 | 14J | 4 nm | 190 μm |
| 12 | 14K | 4 nm | 165 μm |
| 13 | 14L | 4 nm | 220 μm |
| 14 | 14M | 2 nm | 145 μm |
| 15 | 14N | 2 nm | 125 μm |
| 16 | 14O | 2 nm | 142 μm |
| 17 | 14P | 2 nm | 7 μm |

Figure 15C:
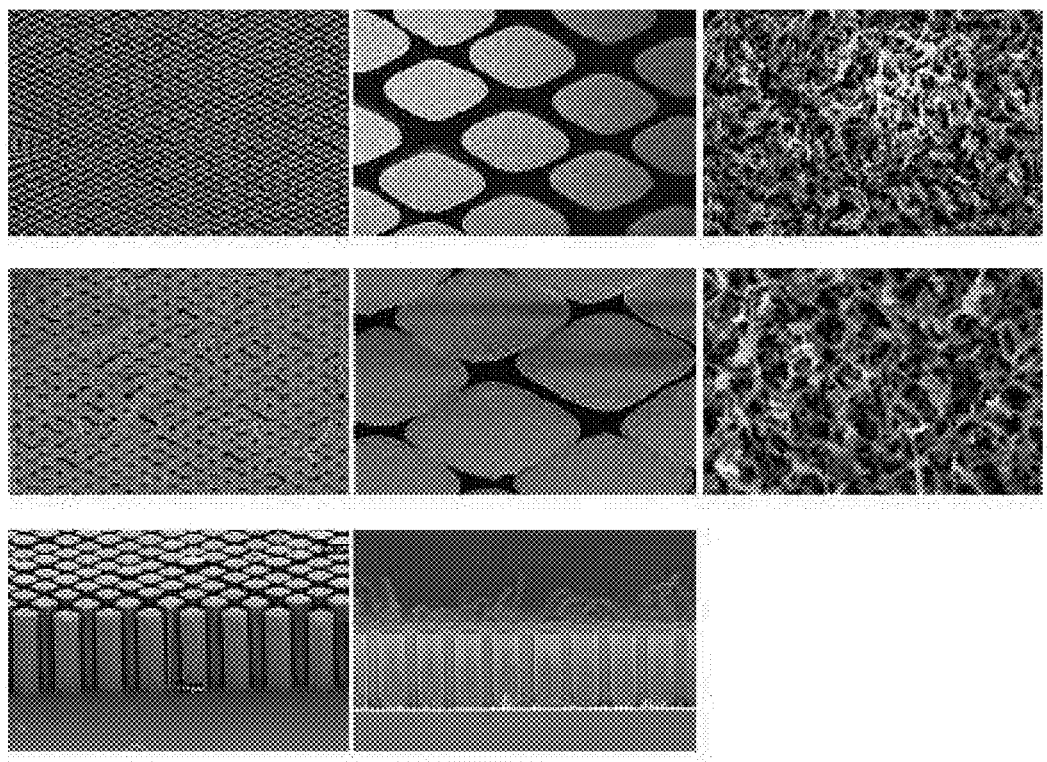
FIGS. 15A-15N show SEM images of silicon infiltrated CNTs, and oxidized elongated nanostructures.
Figure 15D:
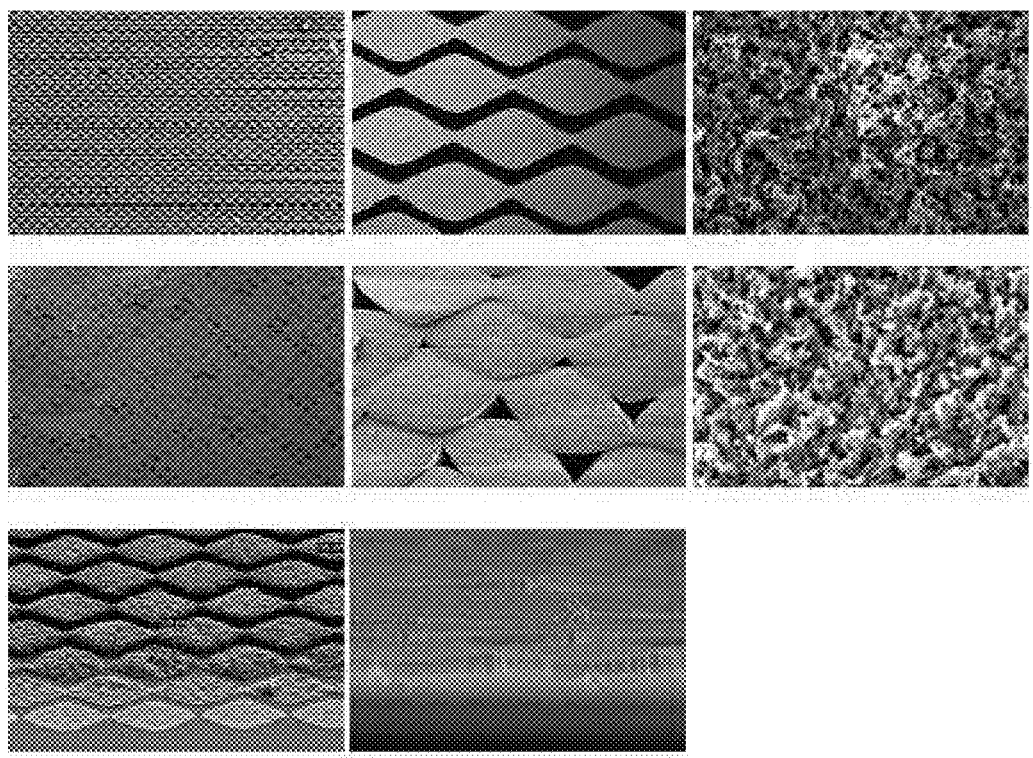
Figure 15E:
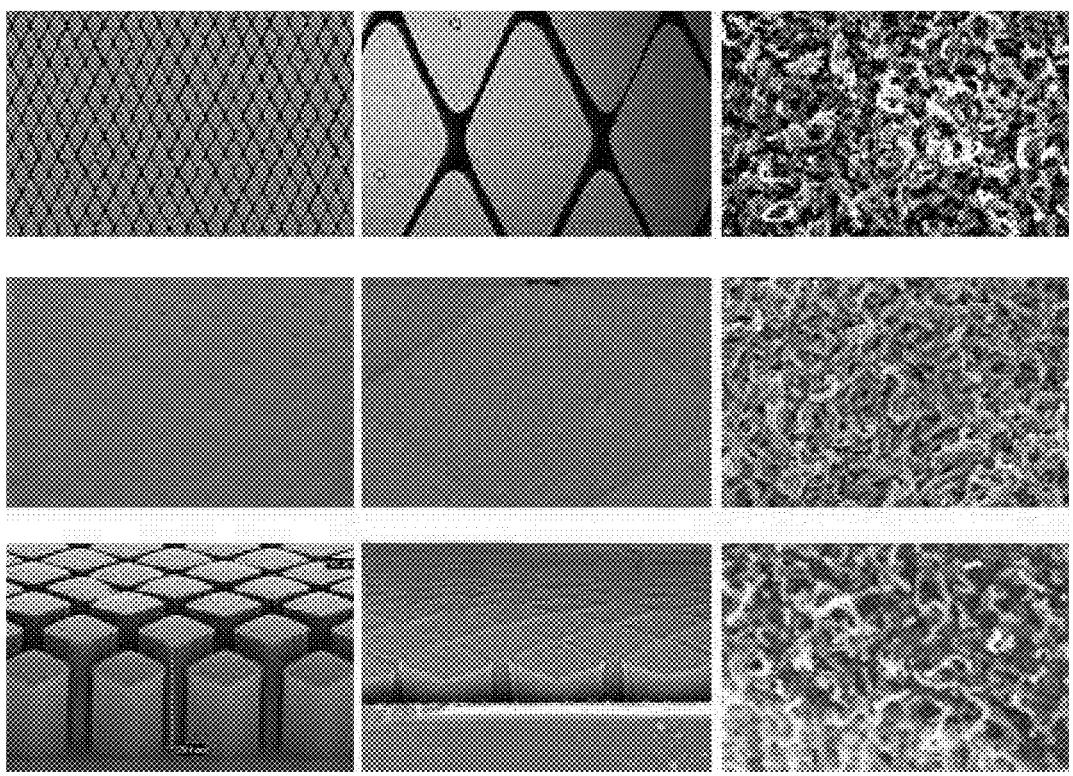
Figure 15F:
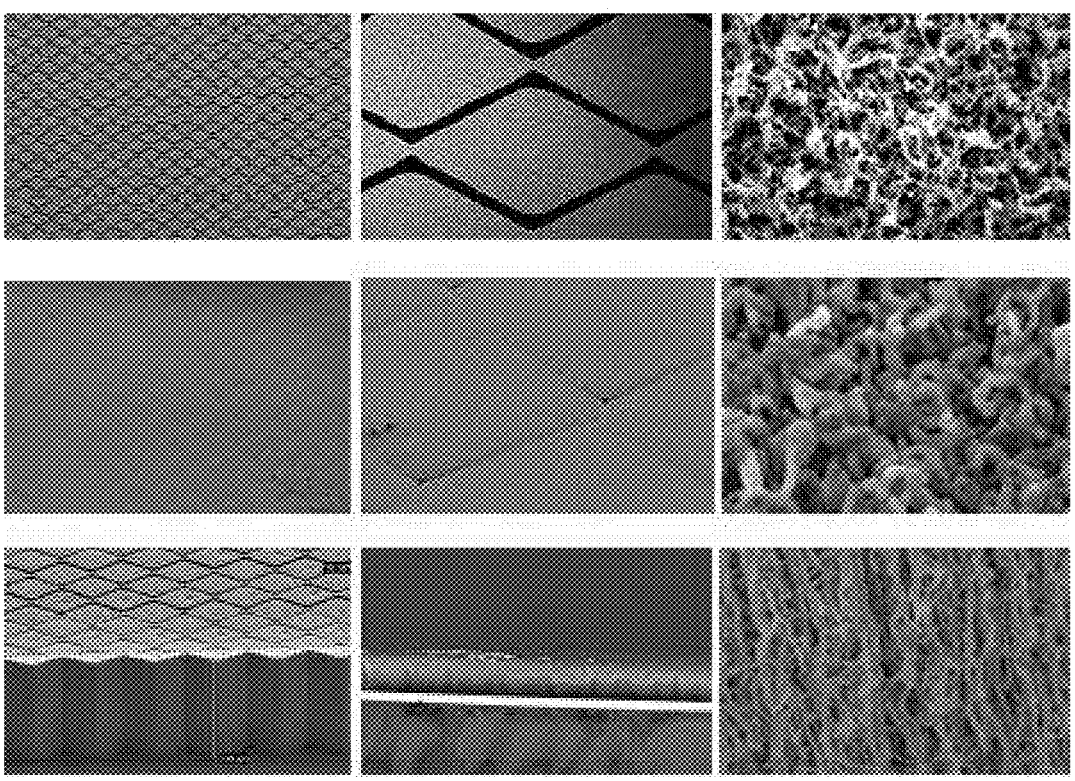
Figure 15G:
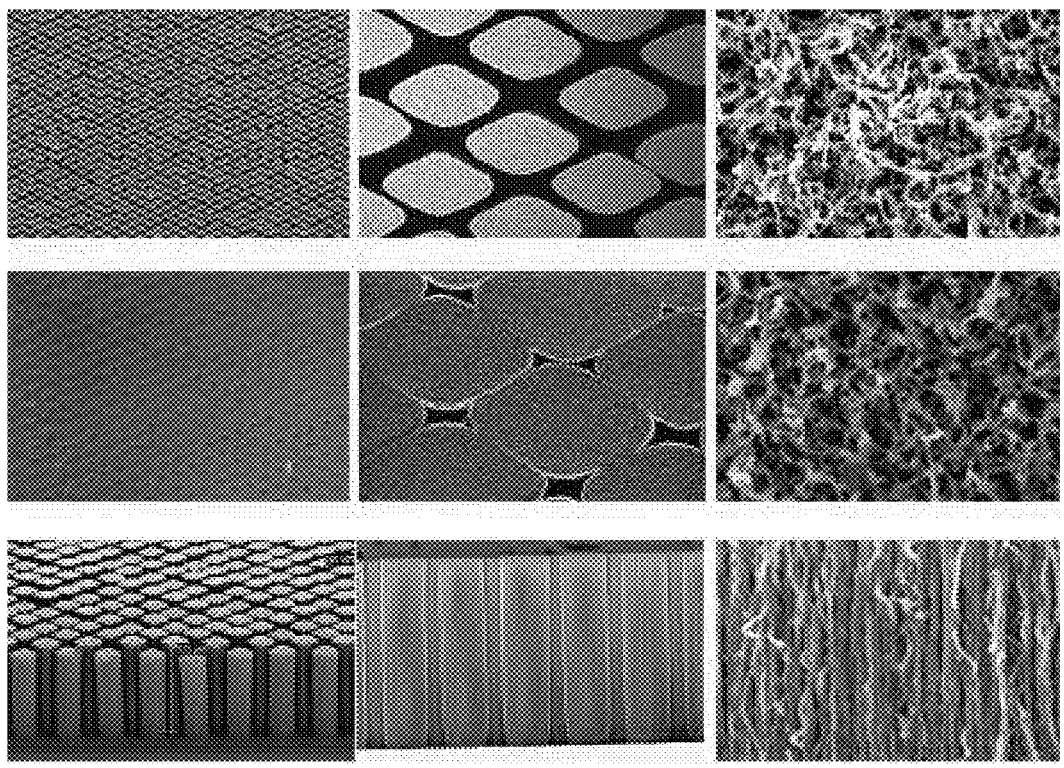
Figure 15H:
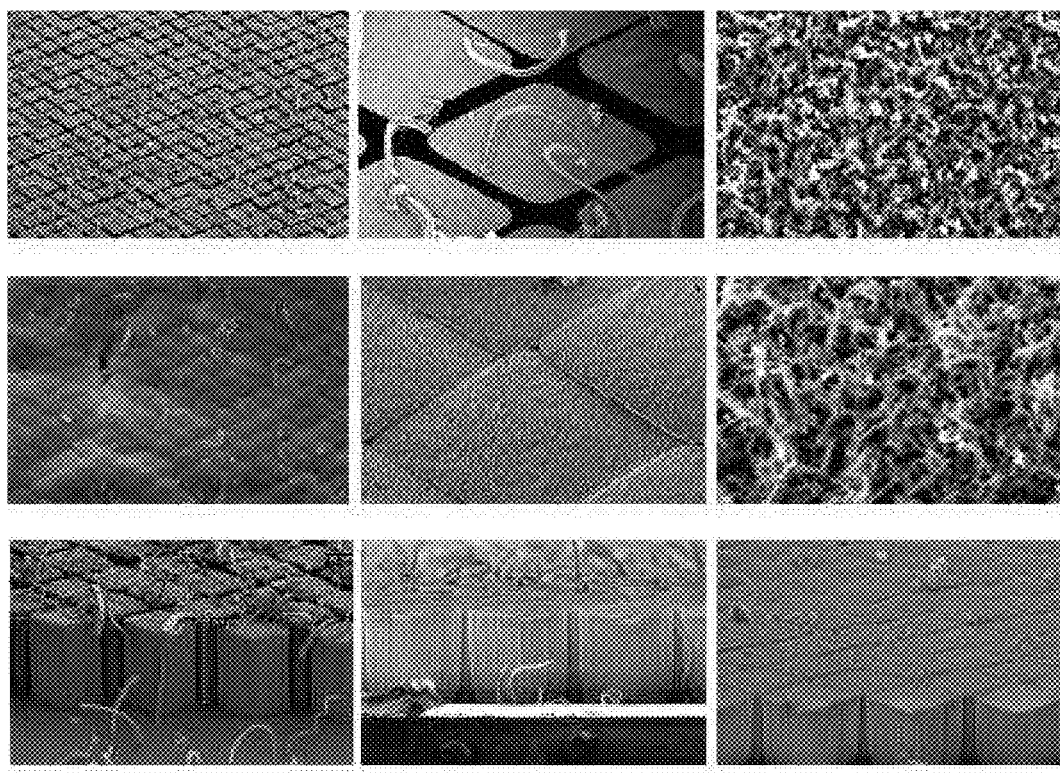
Figure 15I:
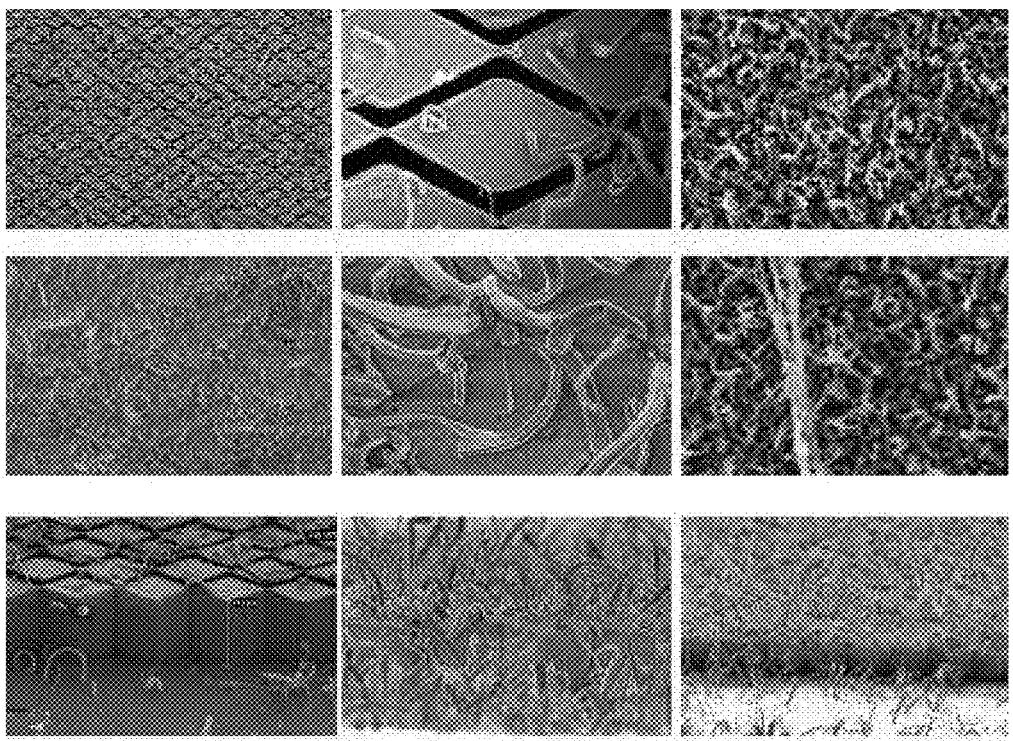
Figure 15J:
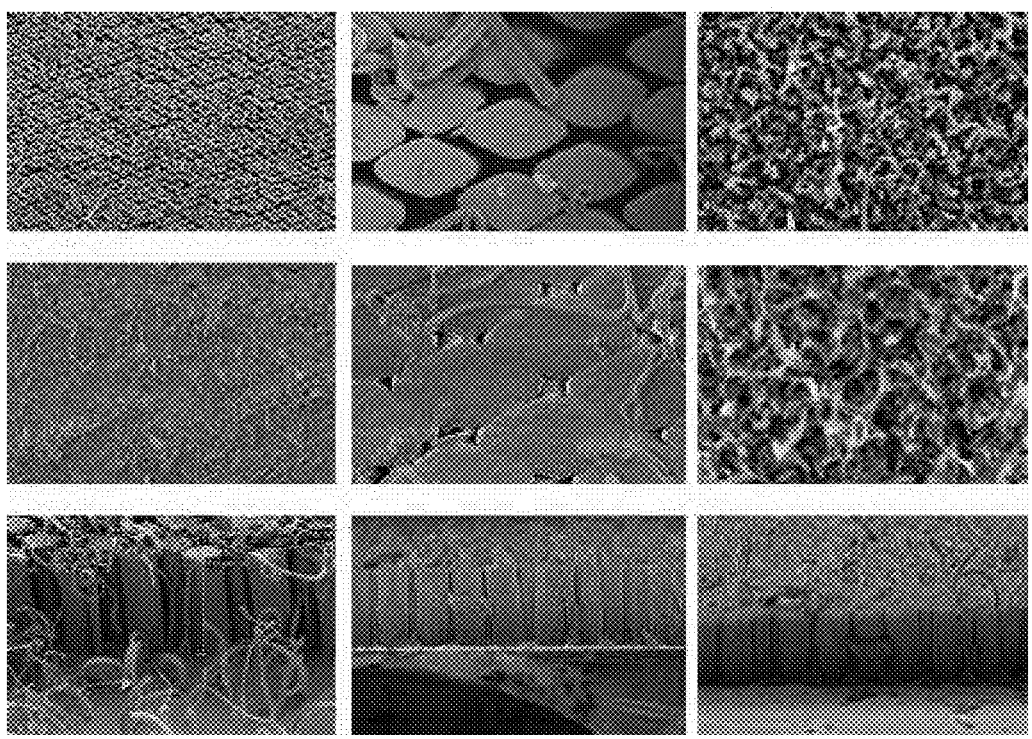
Figure 15K:
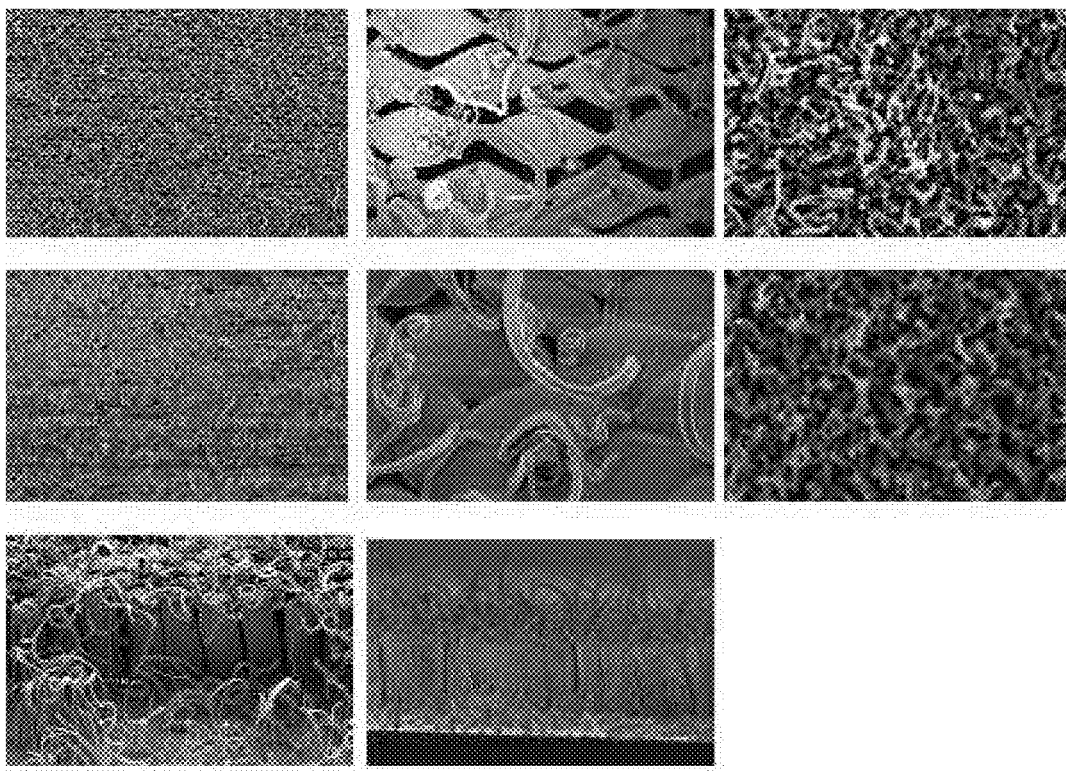
Figure 15L:
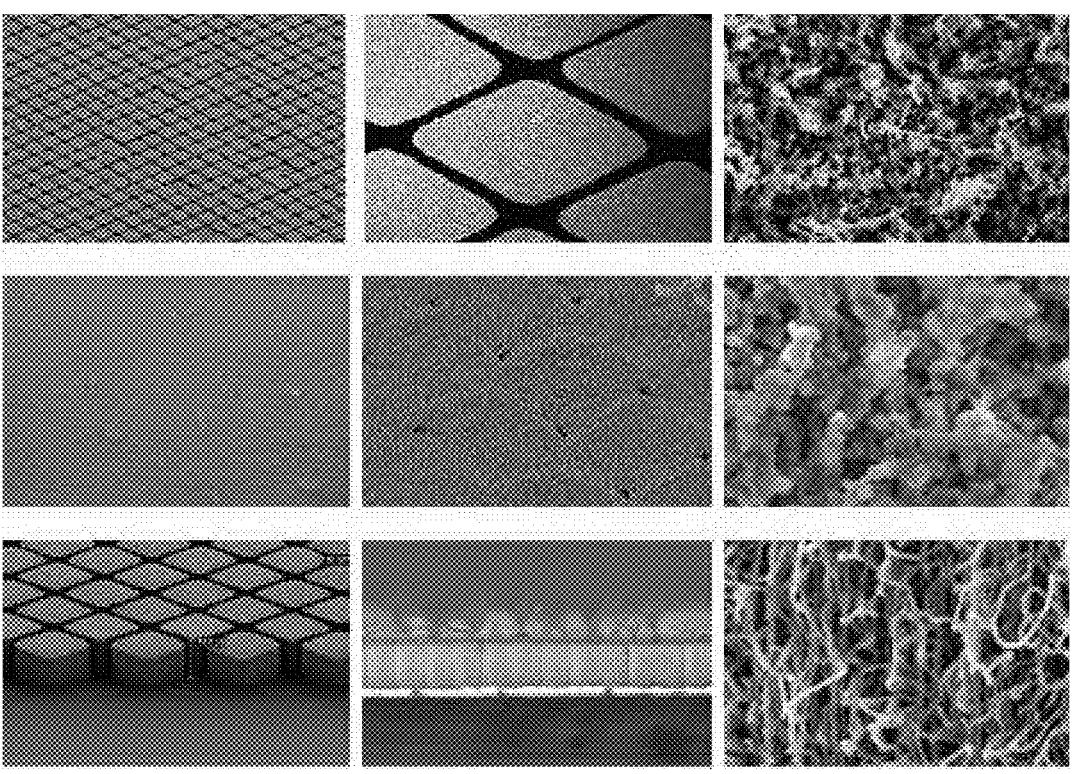
Figure 16A:
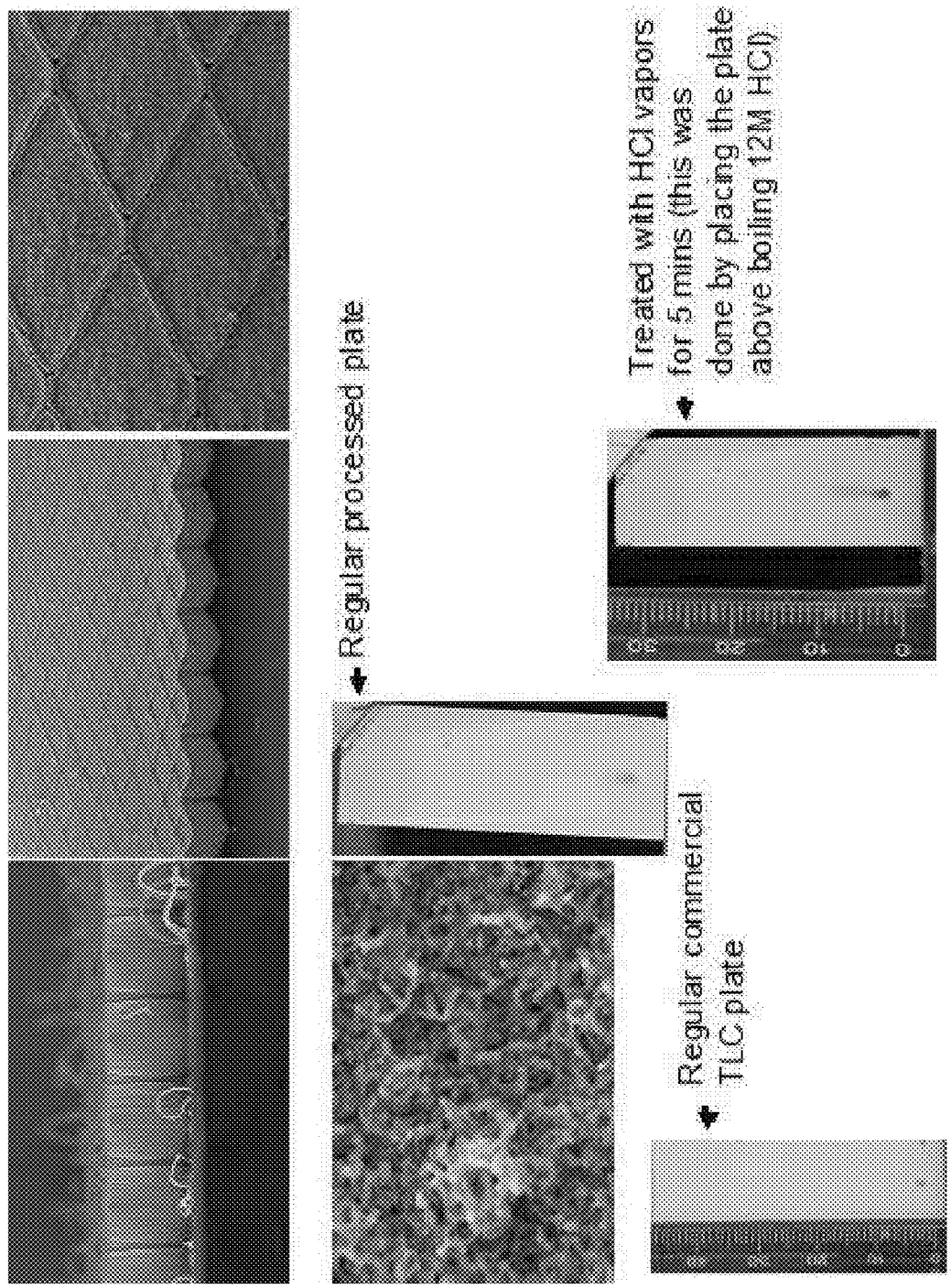
FIGS. 16A-16D show SEM and other images comparing the separation efficiency of various TLC plates.
Figure 16B:
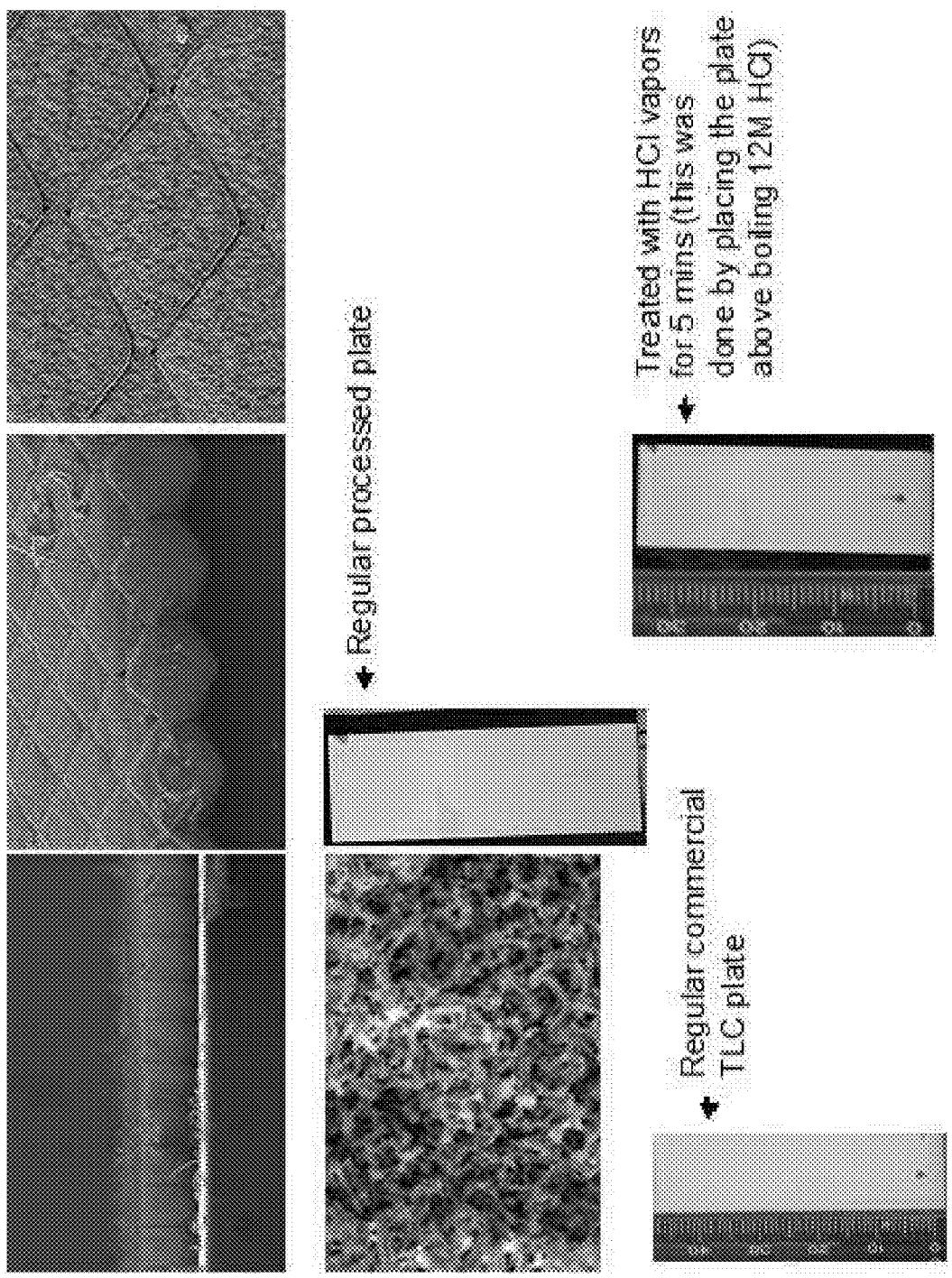
Figure 16C:
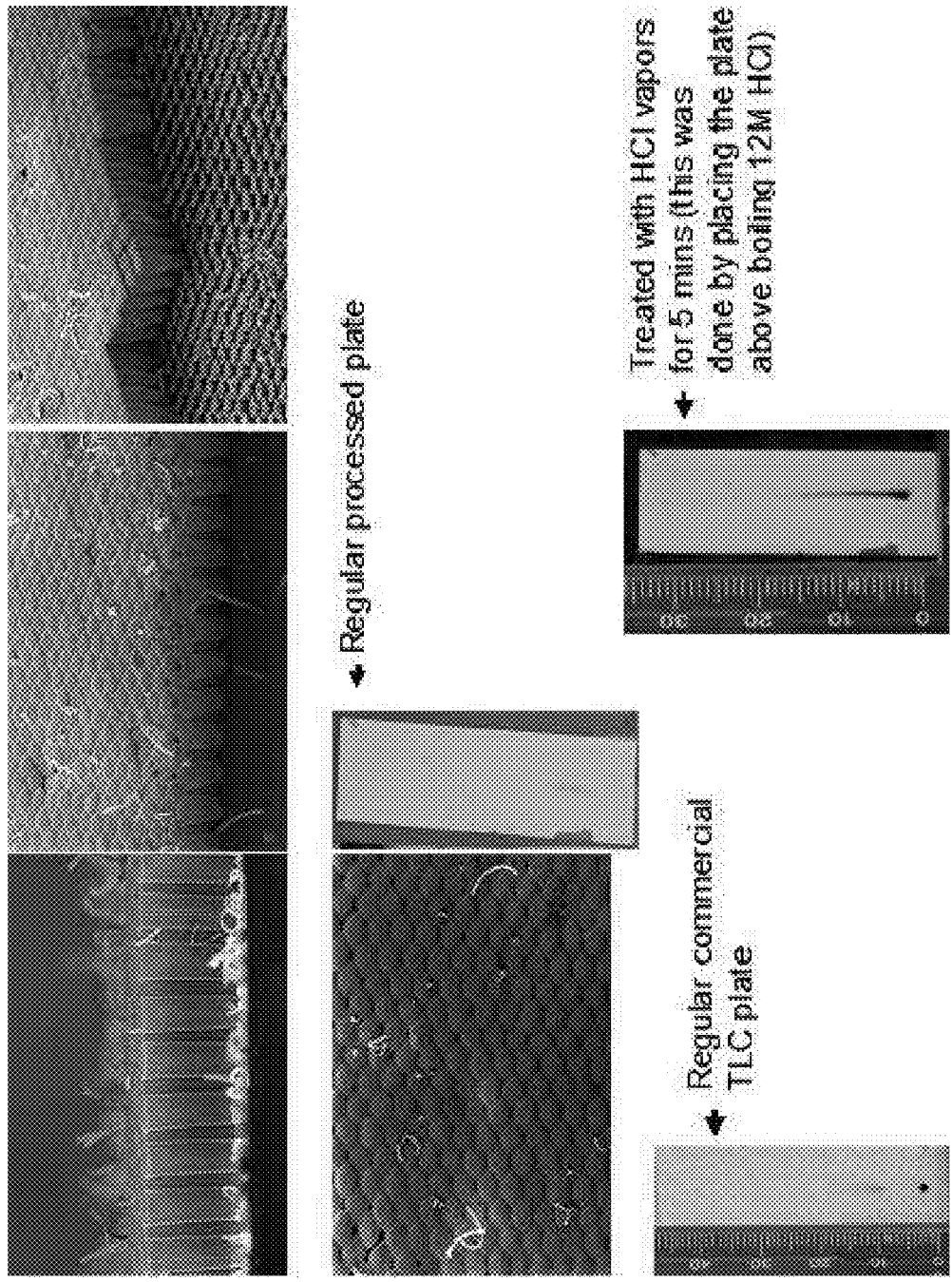
Figure 16D:
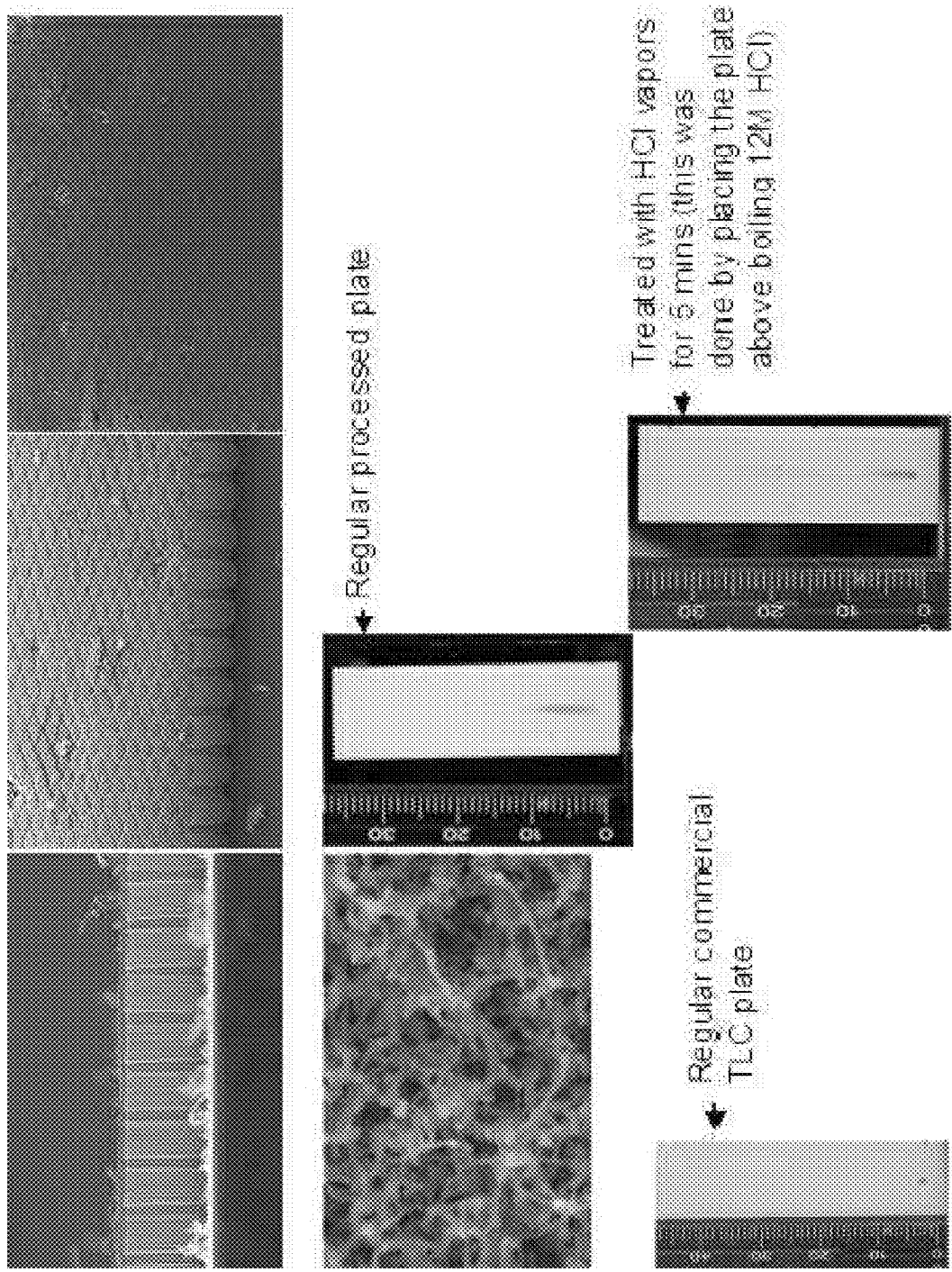

FIGS. 15A-15N are additional SEM images of the prepared examples. Each of FIGS. 15A-15N includes three rows of pictures. The first row of pictures show the silicon infiltrated CNTs, prior to oxidation. The second row of pictures shows the oxidized silicon nanostructures in which the silicon has been oxidized to $SiO_2$. The third row of pictures shows some additional views, in which the first picture is a side perspective view of the silicon nanostructures, the second picture is a side perspective view of the $SiO_2$ nanostructures, and the third picture is a close-up side view of the $SiO_2$ nanostructures. Table II below provides additional information relative to each of these prepared Examples.

TABLE II

| Example | FIGURE | Fe Thickness |
|---|---|---|
| 18 | 15A | 2 nm |
| 19 | 15B | 2 nm |
| 20 | 15C | 2 nm |
| 21 | 15D | 2 nm |
| 22 | 15E | 4 nm |
| 23 | 15F | 4 nm |
| 24 | 15G | 4 nm |
| 25 | 15H | 6 nm |
| 26 | 15I | 6 nm |
| 27 | 15J | 6 nm |
| 28 | 15K | 6 nm |
| 29 | 15L | 7 nm |
| 30 | 15M | 7 nm |
| 31 | 15N | 7 nm |

FIGS. 16A-16D are SEM images of several of the prepared samples, as well as comparative testing results for several of the prepared samples as compared to a commercial TLC plate, a regularly processed TLC plate, and a TLC plate treated with HCl vapors by placing the plate over 12M HCl for 5 minutes. Three different analytes, Rhodamine 6G, Sunset Yellow FCF, and Sulforhodamine B, were used in the comparative testing. The analytes separate in the above listed order in a 9:1 dichloromethane:methanol solvent system. The SEM images show, going from left to right and top to bottom: (1) a side elevation view of the elongated nanostructures; (2) a top perspective view of the elongated nanostructures; (3) a top plan view of the elongated nanostructures; and (4) a close-up view of the elongated nanostructures. Also shown (and labeled) is the comparative testing of a commercial TLC plate, a regularly processed plate (i.e., without hydroxylation of the $SiO_2$), and an HCl treated plate in which the $SiO_2$ is hydroxylated. As seen in the images, the regularly processed plate results in better separation of the analytes than the commercial TLC plate, and the HCl treated plate results in better separation of the analytes than the regularly processed TLC plate. Table III below provides additional information relative to each of these Examples.

TABLE III

| Example | FIGURE | Fe Thickness |
|---|---|---|
| 32 | 16A | 4 nm |
| 33 | 16B | 4 nm |
| 34 | 16C | 4 nm |
| 35 | 16D | 6 nm |

Example 36

Figure 18A:
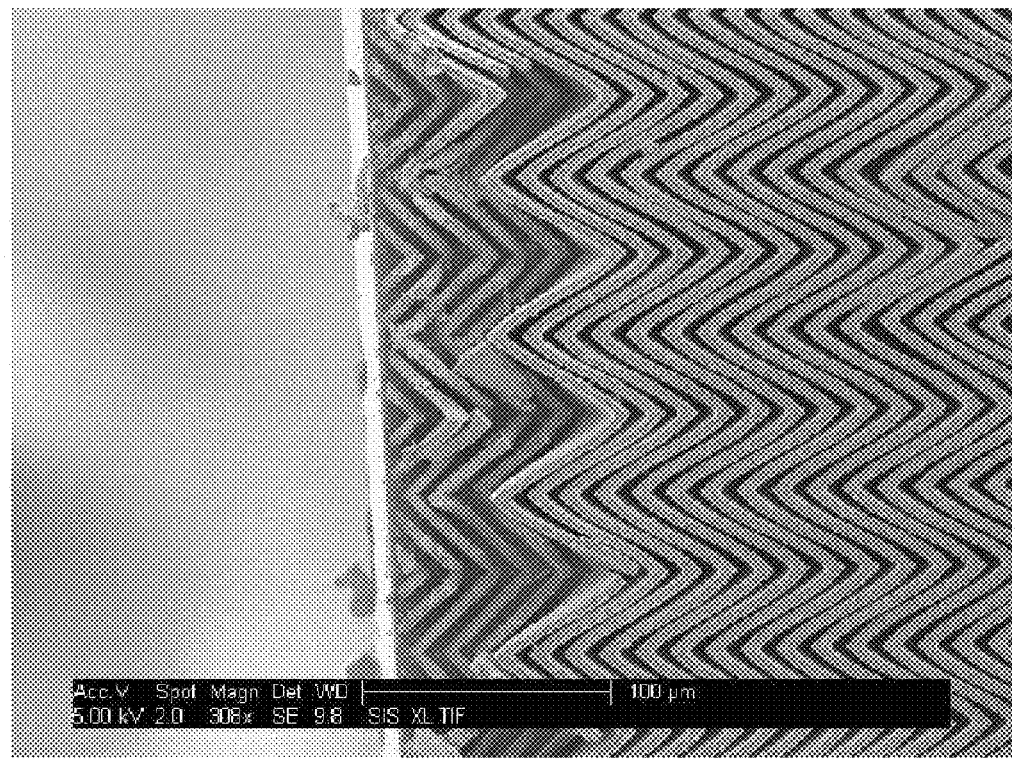
FIG. 18A shows an SEM image of another manufactured TLC plate having $SiO_2$ stationary phase structures having a zigzag configuration.
Figure 18B:
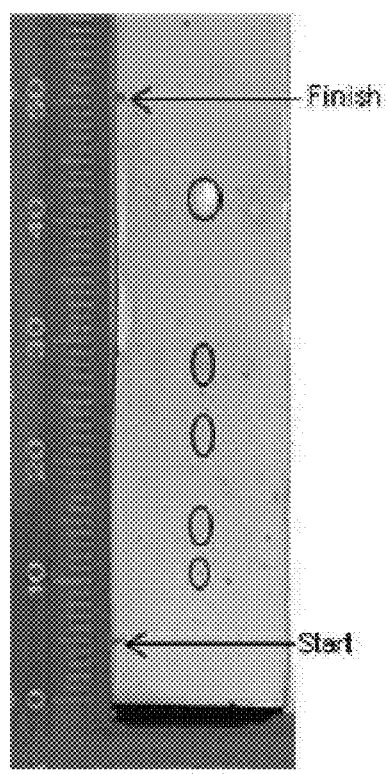
FIG. 18B shows the results of a TLC plate spotted with a CAMAG test mixture.
Figure 18C:
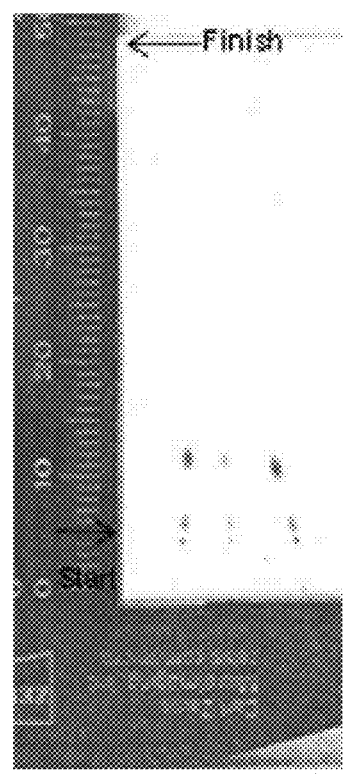
FIG. 18C shows the comparative results of a commercial TLC plate spotted with the CAMAG test mixture.

FIG. 18A is an SEM image showing a substantially continuous zigzag pattern of $SiO_2$ stationary phase structures that were formed. To demonstrate the chromatographic abilities of the TLC plate of FIG. 18A, a test solution produced by CAMAG (Muttenz, Switzerland) was used. As shown in FIG. 18B, the TLC plate spotted with the CAMAG test mixture showed complete resolution of all five analytes. Run distance was 45 mm with the mobile phase of toluene. The $R_f$ values of the colored compounds were as follows: Yellow: 0.933, Red: 0.624, Blue 0.506, Black: 0.32, Purple: 0.231. This plate showed somewhat different selectivity towards the CAMAG test mixture compared to a commercial plate (FIG. 18C). The $R_f$ values of the colored compounds for the commercial plate were as follows: Yellow: 0.260, Red: 0.136, Blue 0.120, Black: 0.098, Purple: 0.002.

The described embodiments may be used in different types of liquid or gas chromatography, such as high-performance liquid chromatography ("HPLC"), ultra-performance liquid chromatography ("UPLC"), microfluidic applications, pressurized liquid chromatography, microfluidic or nanofluidic chromatography, circular or anti-circular TLC, and any other type of chromatography application. Various columns or separations media for HPLC, UPLC, or microfluidic applications containing the patterned or un-patterned infiltrated CNTs are within the scope of the present disclosure.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

What is claimed is:

1. A method for manufacturing a thin layer chromatography plate, the method comprising:
    forming a catalyst layer disposed on a substrate that includes a first portion and at least a second portion, each of the first and at least a second portions exhibiting a selected non-linear configuration;
    forming a layer of elongated nanostructures on the first and at least a second portions of the catalyst layer, wherein the layer of elongated nanostructures includes a first portion grown on the first portion of the catalyst layer and at least a second portion grown on the at least a second portion of the catalyst layer;
    at least partially coating the elongated nanostructures with a coating, the coating including at least one of a stationary phase or a precursor of a stationary phase for use in chromatography; and
    after the act of at least partially coating the elongated nanostructures with a coating, at least partially removing the elongated nanostructures.

2. The method as recited in claim 1, wherein the coating that at least partially coats the elongated nanostructures defines respective elongated structures that extend longitudinally away from the substrate.

3. The method as recited in claim 1, wherein the catalyst layer comprises iron, nickel, copper, cobalt, alloys thereof, or combinations thereof.

4. The method as recited in claim 1, wherein the substrate comprises a backing layer on which the catalyst layer is disposed, the backing layer including at least one material selected from the group consisting of silica, silicon, nickel alumina, borosilicate glass, and steel.

5. The method as recited in claim 1, wherein the catalyst layer exhibits a thickness between about 0.5 nm and about 5 nm.

6. The method as recited in claim 1, wherein forming the layer of elongated nanostructures on the first and at least a second portions of the catalyst layer comprises growing a layer of carbon nanotubes.

7. The method as recited in claim 6, wherein the substrate and the catalyst layer are heated to between about 600° C. and about 900° C. during the act of growing the layer of carbon nanotubes.

8. The method as recited in claim 1, wherein at least partially coating the elongated nanostructures with a coating comprises forming the coating to include at least one material selected from the group consisting of silicon, silicon dioxide, silicon nitride, aluminum, aluminum oxide, titanium, titanium oxide, zirconium, and zirconium oxide.

9. The method as recited in claim 8, wherein forming the coating to include at least one material selected from the group consisting of silicon, silicon dioxide, silicon nitride, aluminum, aluminum oxide, titanium, titanium oxide, zirconium, and zirconium oxide comprises at least partially infiltrating the elongated nanostructures by low pressure chemical vapor deposition with an infiltrant.

10. The method as recited in claim 9, wherein the low pressure chemical vapor deposition process is carried out at a temperature between about 500° C. and about 650° C. and a pressure between about 100 mTorr and about 300 mTorr.

11. The method as recited in claim 1, wherein at least partially removing the elongated nanostructures comprises oxidizing the coating that at least partially coats the elongated nanostructures so that a plurality of stationary phase structures are formed and oxidizing the elongated nanostructures so that the elongated nanostructures are substantially removed.

12. The method as recited in claim 11, further comprising functionalizing the plurality of stationary phase structures.

13. The method as recited in claim 1, further comprising heating the elongated nanostructures in an oxidizing environment so that the elongated nanostructures are substantially removed.

14. The method as recited in claim 1, wherein each of the first and at least a second portions of the catalyst layer form a zigzag pattern.

* * * * *